United States Patent
Kobayashi et al.

(10) Patent No.: US 7,755,749 B2
(45) Date of Patent: Jul. 13, 2010

(54) SUPERCONDUCTING WIRE INSPECTION APPARATUS AND METHOD

(75) Inventors: Shinichi Kobayashi, Osaka (JP); Noritsugu Hamada, Hyogo (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 351 days.

(21) Appl. No.: 11/887,330

(22) PCT Filed: Apr. 6, 2006

(86) PCT No.: PCT/JP2006/307340

§ 371 (c)(1),
(2), (4) Date: Sep. 27, 2007

(87) PCT Pub. No.: WO2006/115007

PCT Pub. Date: Nov. 2, 2006

(65) Prior Publication Data

US 2009/0135412 A1     May 28, 2009

(30) Foreign Application Priority Data

Apr. 21, 2005     (JP)     ............... 2005-123634

(51) Int. Cl.
*G01N 21/00* (2006.01)
(52) U.S. Cl. .................. 356/237.1; 356/430
(58) Field of Classification Search ............ 356/430, 356/429
See application file for complete search history.

(56) References Cited

U.S. PATENT DOCUMENTS

| | | | | |
|---|---|---|---|---|
| 4,705,957 A | * | 11/1987 | Puffer et al. | 250/559.03 |
| 5,293,220 A | * | 3/1994 | Fukuda et al. | 356/394 |
| 5,621,218 A | * | 4/1997 | Tanaka | 250/559.34 |
| 5,654,554 A | * | 8/1997 | Feller et al. | 250/559.45 |
| 6,046,764 A | * | 4/2000 | Kirby et al. | 348/92 |
| 6,166,393 A | | 12/2000 | Paul et al. | |

(Continued)

FOREIGN PATENT DOCUMENTS

JP     6-221833 A     8/1994

(Continued)

OTHER PUBLICATIONS

L. Masur et al., "Long Length Manufacturing of High Performance BSCCO-2223 Tape for the Detroit Edison Power Cable Project," IEEE Transactions on Applied Superconductivity, vol. 11, No. 1, 2001 p. 3256-3260.

(Continued)

*Primary Examiner*—Roy Punnoose
(74) *Attorney, Agent, or Firm*—Foley & Lardner LLP

(57) ABSTRACT

An apparatus inspecting a superconducting wire includes: a blue LED emitting light in a direction normal to a front surface of a superconducting wire to illuminate the front surface; a red LED emitting light in a direction forming an angle with the direction normal to the front surface of the superconducting wire to illuminate the front surface; a color line sensor mainly receiving light reflected by the superconducting wire, and mainly receiving light diffused by the superconducting wire; and a computer accumulating and outputting a quantity of light received by the color line sensor. The apparatus can inspect with high sensitivity whether the superconducting wire has a defect or not.

17 Claims, 19 Drawing Sheets

U.S. PATENT DOCUMENTS

| | | | |
|---|---|---|---|
| 6,453,264 B1 * | 9/2002 | Maguire et al. | 702/172 |
| 6,496,271 B1 * | 12/2002 | Ngo | 356/613 |
| 6,597,455 B1 * | 7/2003 | Wlodarski et al. | 356/430 |
| 7,307,729 B2 * | 12/2007 | Moshe | 356/430 |
| 7,495,766 B2 * | 2/2009 | Butler et al. | 356/429 |
| 2002/0036770 A1 * | 3/2002 | Maeda | 356/237.1 |
| 2003/0020916 A1 * | 1/2003 | Ghilai et al. | 356/445 |
| 2004/0237294 A1 | 12/2004 | Kobayashi et al. | |
| 2007/0246643 A1 * | 10/2007 | Fardeau | 250/222.1 |

FOREIGN PATENT DOCUMENTS

| | | | |
|---|---|---|---|
| JP | 8-247965 A | | 9/1996 |
| JP | 11-515108 A | | 12/1999 |
| JP | 2001-514386 A | | 9/2001 |
| JP | 3308619 (B2) | * | 7/2002 |
| JP | 2002-243427 A | | 8/2002 |
| WO | WO-98/10271 A1 | | 3/1998 |
| WO | WO-99/01073 A1 | | 3/1999 |
| WO | WO-03/100795 A1 | | 12/2003 |

OTHER PUBLICATIONS

Japanese Patent Office; International Search Report for PCT/JP2006/307340; Mailing date Jul. 25, 2006.

L. Masur et al., "Long Length Manufacturing of High Performance BSCCO-2223 Tape for the Detroit Edison Power Cable Project," *IEEE Transactions on Applied Superconductivity*, vol. 11, No. 1, 2001 pp. 3256-3260.

Office Action dated Aug. 24, 2009 from corresponding Korean application.

English Translation of Korean Office Action dated Aug. 24, 2009.

* cited by examiner

SUPERCONDUCTING WIRE INSPECTION APPARATUS AND METHOD

TECHNICAL FIELD

The present invention relates generally to superconducting wire inspection apparatuses and methods and particularly to such apparatuses and methods capable of inspecting defects of superconducting wires with high sensitivity.

BACKGROUND ART

Superconducting cables and similar superconducting equipment are configured of a large number of superconducting wires. When superconducting equipment is used, it has its internal superconducting filament(s) cooled to a critical temperature ($T_c$) or lower and to do so the superconducting equipment is immersed for example in liquid nitrogen, liquid helium or a similar liquid coolant and held at cryogenic temperature. In contrast, if the superconducting equipment is for example inspected, it is extracted from the liquid coolant and a gaseous coolant or the like having room temperature is introduced to surround the superconducting equipment to increase the superconducting equipment in temperature from cryogenic temperature to room temperature. Increasing the superconducting equipment having been immersed in the liquid coolant in temperature to room temperature, however, causes a superconducting wire, a constituent thereof, to balloon.

Ballooning is such a phenomenon that as temperature increases, a liquid coolant having entered a superconducting wire is gasified and not discharged externally, and as a result the superconducting wire's internal pressure increases and the superconducting wire thus expands. Ballooning is caused as follows: when superconducting equipment is immersed in a liquid coolant, the liquid coolant enters a superconducting wire through a pin hole or a similar defect existing in a surface of the wire, and as temperature increases, the liquid coolant is gasified and expands. If a balloon is caused at a portion the portion has a superconducting wire with a current path disrupted and thus invites an impaired critical current value and/or a similarly impaired superconducting characteristic(s). The phenomenon of ballooning is disclosed for example by L. Masur, et al., "Long Length Manufacturing of High Performance BSCCO-2223 Tape for the Detroit Edison Power Cable Project" (Non-Patent Document 1).

In order to prevent ballooning, before a superconducting wire is actually used an whether the superconducting wire has a defect or not is inspected. One such inspection (or test) is a test employing pressurized nitrogen. In this test, a superconducting wire is immersed for a predetermined period of time in a liquid coolant pressurized to approximately 1 MPa. The wire is thus cooled, and subsequently increased in temperature rapidly to room temperature and inspected for whether it has ballooning. In the test, whether a superconducting wire has ballooning or not is inspected to determine whether the wire is a defective wire.

Non-Patent Document 1: L. Masur, et al., "Long Length Manufacturing of High Performance BS CCO-2223 Tape for the Detroit Edison Power Cable Project", IEEE Trans. Appl. Superconductivity., vol. 11, No. 1 pp. 3256-3260.

DISCLOSURE OF THE INVENTION

Problems to be Solved by the Invention

The test employing pressurized nitrogen, however, is disadvantageous in that whether a superconducting wire has a defect or not cannot be inspected with high sensitivity. As has been described above, in the test, a superconducting wire is immersed in a liquid coolant for a predetermined period of time to introduce the liquid coolant into the wire if the wire has a defect. If the wire has a small defect, however, it will take time to introduce the liquid coolant into the wire through the defect. As such, the wire having the small defect undergoing the test and thus immersed for the predetermined period of time cannot introduce the liquid coolant thereinto sufficiently and thus may not balloon. Furthermore, there is also a case in which ballooning does not occur despite that the test is repeatedly conducted.

Electricity transmission and distribution cables and similar superconducting equipment are required to endure use over several tens years. In such use, even a small defect can be a cause of ballooning. Accordingly, it is necessary to also detect small defects with high sensitivity.

Accordingly the present invention contemplates a superconducting wire inspection apparatus and method capable of inspecting with high sensitivity whether a superconducting wire has a defect.

Means for Solving the Problems

The present invention in one aspect provides an apparatus inspecting a superconducting wire, including: an illumination unit emitting light to illuminate a superconducting wire; a photoreceptive unit receiving light from the superconducting wire; and an output unit accumulating and outputting a quantity of light received by the photoreceptive unit.

The present method of inspecting a superconducting wire includes the steps of: emitting light to illuminate a superconducting wire; receiving light from the superconducting wire; and accumulating and outputting a quantity of light received.

In the present superconducting wire inspection apparatus and method in one aspect the light reflected by a superconducting wire at a defective portion and that reflected by the superconducting wire at a defectless portion are reflected in mutually different directions regardless of whether the defect is large or small. Accordingly there is received light varying in quantity with whether there is defect or not, and from such variation in quantity of light, whether there is a defect or not can be inspected. This allows even a small defect to be also detected, and the superconducting wire can be inspected for defects with high sensitivity.

In the above apparatus preferably the photoreceptive unit is a photoreceptive unit receiving a reflection of light, that mainly receives light reflected by the superconducting wire.

In the above method preferably the step of receiving includes mainly receiving the light reflected by the superconducting wire.

The light reflected by the superconducting wire varies in quantity with whether there is a defect or not, and from such variation in quantity of light, whether there is a defect or not can be inspected with high sensitivity. Note that the light reflected by a superconducting wire indicates that reflected by the superconducting wire at a defectless portion.

In the above apparatus preferably the photoreceptive unit is a photoreceptive unit receiving diffused light, that mainly receives light diffused by the superconducting wire.

In the above method preferably the step of receiving includes mainly receiving the light diffused by the superconducting wire.

The light diffused by the superconducting wire varies in quantity with whether there is a defect or not, and from such variation in quantity of light, whether there is a defect or not can be inspected with high sensitivity. Note that light diffused by a superconducting wire indicates light diffused by the superconducting wire at a defective portion in various directions.

In the above apparatus preferably the illumination unit is a coaxial illumination unit emitting light in a direction normal to a front surface of the superconducting wire to illuminate the front surface.

In the above method preferably the step of emitting includes emitting light in a direction normal to a surface of the superconducting wire.

This can particularly help to detect a flaw in a surface of the superconducting wire.

In the above apparatus preferably the illumination unit is an oblique illumination unit emitting light in a direction forming an angle with a direction normal to a front surface of the superconducting wire to illuminate the front surface.

In the present method preferably the step of emitting includes emitting light in a direction forming an angle with a direction normal to a surface of the superconducting wire.

This can particularly help to detect whether the superconducting wire has a pinhole.

The above apparatus preferably further includes a laser displacement sensor including a laser light illumination unit emitting a laser beam of light to illuminate the superconducting wire while moving relative to the superconducting wire in a longitudinal direction of the superconducting wire, a laser light reception unit receiving a laser beam of light reflected by the superconducting wire, and an output unit associated with the laser displacement sensor and outputting information on displacement of the superconducting wire as based on at which position the laser light reception unit receives light.

The above apparatus preferably further includes an eddy current displacement sensor including: an alternate current generation unit passing an alternate current through a coil associated with the eddy current displacement sensor; the coil associated with the eddy current displacement sensor and generating an eddy current in the superconducting wire while moving relative to the superconducting wire in a longitudinal direction of the superconducting wire; and an output unit associated with the eddy current displacement sensor and outputting information on displacement of the superconducting wire as based on such variation in how the coil associated with the eddy current displacement sensor oscillates that is caused as the eddy current is generated.

The above apparatus preferably further includes a contact displacement sensor including a probe moving relative to the superconducting wire in a longitudinal direction of the superconducting wire in contact with the superconducting wire and also moving in accordance with displacement of the superconducting wire, an iron core attached to the probe, a coil associated with the contact displacement sensor and generating an induced electromotive force as the iron core moves, and an output unit associated with the contact displacement sensor and outputting information on displacement of the superconducting wire as based on the induced electromotive force.

The above method preferably further includes the steps of emitting a laser beam of light in a longitudinal direction of the superconducting wire to illuminate the wire; receiving the laser beam of light reflected by the superconducting wire; and outputting information on displacement of the superconducting wire as based on a position receiving the laser beam of light.

The above method preferably further includes the steps of: employing a coil associated with an eddy current displacement sensor and receiving and passing an alternate current therethrough to generate an eddy current in the superconducting wire in a longitudinal direction of the superconducting wire; and outputting information on displacement of the superconducting wire as based on such variation in how the coil associated with the eddy current displacement sensor oscillates that is caused as the eddy current is generated.

The above method preferably further includes the steps of: moving a probe, having an iron core attached thereto, relative to the superconducting wire in contact with the superconducting wire in a longitudinal direction of the superconducting wire, and also allowing the probe to move in accordance with displacement of the superconducting wire; and generating an induced electromotive force in a coil, which is associated with a contact displacement sensor, as the iron core moves, and outputting information on displacement of the superconducting wire as based on the induced electromotive force.

Information on displacement of the superconducting wire can be obtained, and blister, bending, local variation in width, deformation and similar defects, in particular, can be detected with high sensitivity. Furthermore, not only whether there is a defect or not but also the defect's size, geometry and the like can be measured. As a result, the superconducting wire can be inspected more effectively.

The above apparatus preferably further includes first to third barycenter measuring devices aligned in a longitudinal direction of the superconducting wire to measure a center of the superconducting wire as seen widthwise.

The above method preferably further includes the steps of: measuring a center of the superconducting wire, as seen widthwise, at a first position; measuring a center of the superconducting wire, as seen widthwise, at a second position different from the first position in a longitudinal direction of the wire; and measuring a center of the superconducting wire, as seen widthwise, at a third position different from the first and second positions in the longitudinal direction of the wire.

Thus whether three centers exist at identical positions as seen widthwise can be determined to measure whether the superconducting wire has gentle widthwise deformation, such as deflection, waviness, swelling and the like.

The present invention in another aspect provides an apparatus inspecting a superconducting wire, including: a coaxial illumination unit emitting light in a direction normal to a front surface of a superconducting wire to illuminate the front surface; an oblique illumination unit emitting light in a direction forming an angle with the direction normal to the front surface of the superconducting wire to illuminate the front surface; a photoreceptive unit receiving a reflection of light, that mainly receives a light reflected by the superconducting wire; a photoreceptive unit receiving diffused light, that mainly receives light diffused by the superconducting wire; and an output unit accumulating and outputting a quantity of light received by the photoreceptive unit receiving the reflection of light and the photoreceptive unit receiving the diffused light.

In the present superconducting wire inspection apparatus the light reflected by a superconducting wire at a defective portion and that reflected by the superconducting wire at a defectless portion are reflected in mutually different directions regardless of whether the defect is large or small. Accordingly there is received light varying in quantity with whether there is defect or not, and from such variation in quantity of light, whether there is a defect or not can be inspected. This allows even a small defect to be also detected, and the superconducting wire can be inspected for defects with high sensitivity. In particular, when the photoreceptive unit including both that receiving a reflection of light and that receiving diffused light is compared with only a single photoreceptive unit, the former can facilitate to detect variation in quantity of light. As a result, a defect can be detected with good precision. Furthermore, the illumination unit including a coaxial illumination unit and an oblique illumination unit can help to detect both a flaw in a surface of the superconducting wire and a pinhole in the superconducting wire.

The present invention in one and another aspects provides an inspection apparatus preferably including more than one apparatus described above. This allows a superconducting wire to have a surface inspected in various directions simultaneously and hence more efficiently. In particular, if a superconducting wire in the form of tape is inspected, two such apparatuses can be employed to inspect the wire's upper and lower surfaces simultaneously.

EFFECTS OF THE INVENTION

The present superconducting wire inspection apparatus and method can inspect with high sensitivity whether a superconducting wire has a defect.

BRIEF DESCRIPTION OF THE DRAWINGS

FIG. 26(a) shows a discolored portion and a pinhole and FIG. 26(b) shows a flaw in a surface.

DESCRIPTION OF THE REFERENCE SIGNS 1, 1a: blue LED, 2, 2a: red LED, 3, 3a: color line sensor, 5, 5a, 45, 75: computer, 7, 7a: mirror, 10: optical inspection apparatus, 13: photo receptive window, 20, 40a, 40b: superconducting wire, 20a: a front surface of a superconducting wire, 20b: a back surface of a superconducting wire, 20c: an end surface of a superconducting wire, 21: oxide superconductor filament, 22: sheath, 23, 46, 55, 68: blister, 24: bending, 25: edge, 27: a flaw in a surface, 28: discolored portion, 29: pinhole, 30: superconducting cable, 31: cable core, 32: foamer, 34: insulating paper, 35: kraft paper, 37: coolant path, 38: insulating pipe, 39: anti-corrosion layer, 41: laser displacement sensor, 42: sensor head, 43: semiconductor laser, 44: PSD, 51: eddy current displacement sensor, 52, 64: probe, 52a: coil, 53, 66: main body, 54: eddy current, 56, 57: oscillating waveform, 58: magnetic field, 61: contact displacement sensor, 62a, 62b: secondary coil, 63: primary coil, 65: iron core, 67: casing, 67a: hollow portion, 71-73: barycenter measuring device, 74a: illumination unit, 74b: photoreceptive unit, 76: deflection, 81: feed reel, 82: take up reel, A1-A4: light for illumination, B1-B3: reflection of light, C, C2, C4: diffused light, D, E, E1, E2, F1-F3: laser light, G1: pattern of light received, H1-H3: position of center, L: straight line, P1, P2: position.

BEST MODES FOR CARRYING OUT THE INVENTION

Hereinafter embodiments of the present invention will be described with reference to the drawings.

First Embodiment

Figure 1:
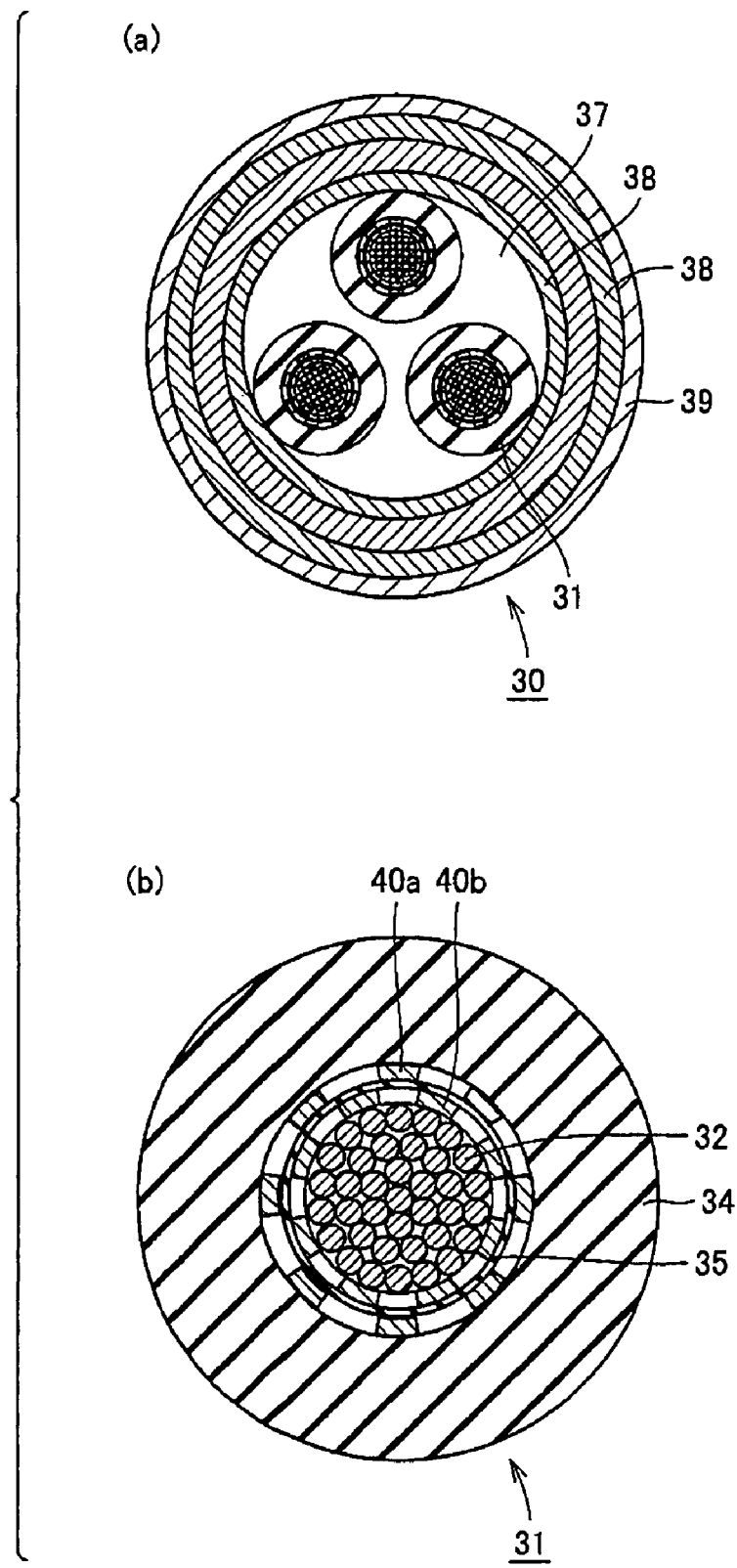
FIG. 1(a) is a cross section of one example of a superconducting cable and FIG. 1(b) is an enlarged view of a cable core in FIG. 1(a).

FIG. 1(a) is a cross section of one example of a superconducting cable and FIG. 1(b) is an enlarged view of a cable core shown in FIG. 1(a). With reference to FIGS. 1(a) and 1(b) a superconducting cable 30 includes a cable core 31, an insulation tube 38, and an anti-corrosion layer 39. Cable core 31, formed of a single filament or multiple filaments stranded together, is inserted in a coolant path 37 provided internal to insulation tube 38 and anti-corrosion layer 39, and a coolant is passed through coolant path 3 around a circumference of cable core 31. Cable core 31 is formed, as seen at inside toward outside, of a roamer (a plurality of copper wires twined together) 32, a plurality of superconducting wires 40a, kraft paper 35, a plurality of superconducting wires 40b, and insulation paper 34. Foamer 32, formed of the plurality of copper twined wires having an outer diameter for example of 20 mm, has a circumference with superconducting wires 40a and 40b in the form of tape each spirally wound therearound. Superconducting wires 40a and 40b are stacked in layers insulated from each other with kraft paper 35 posed therebetween. The plurality of superconducting wires 40a, serving as an underlying layer, are implemented for example by 13 superconducting wires arranged with a pitch of 200 mm. Furthermore, the plurality of superconducting wires 40b, serving as an overlying layer, are implemented for example by 14 superconducting wires arranged with a pitch of 200 mm. Superconducting wires 40a and 40b each have a cross section for example of a rectangle having a longitudinal dimension of 0.21 mm and a lateral dimension of 4.1 mm. The overlying superconducting wire 40b has an outer side covered with insulation paper 34 formed for example of polypropylene laminated paper (PPLP®).

A superconducting wire configuring a superconducting cable will be described hereinafter.

Figure 2:
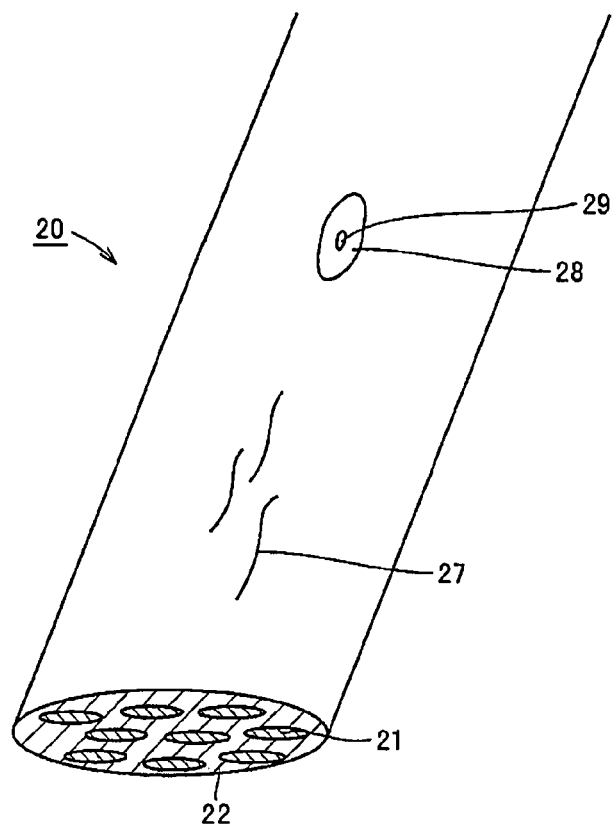
FIG. 2 schematically shows a pinhole or a similar defect caused in a superconducting wire.

FIG. 2 schematically shows a pinhole or a similar defect caused in a superconducting wire. With reference to FIG. 2, a superconducting wire implemented by a multi-filamentary, superconducting oxide wire will now be described by way of example. A superconducting wire 20 corresponds to superconducting wire 40a, 40b shown in FIG. 1 and is for example a superconducting wire of oxide in the form of tape. Superconducting wire 20 has a plurality of longitudinally extending oxide superconductor filaments 21 and a sheath 22 covering the plurality of oxide superconductor filaments 21. The plurality of oxide superconductor filaments 21 are each formed of a material for example having a Bi—Pb—Sr—Ca—Cu—O-based composition and including a Bi2223 phase with a (bismuth and lead):strontium:calcium:copper atomic ratio represented, as approximated, by a ratio of 2:2:2:3. Sheath 22 is formed for example of silver.

Herein, superconducting wire 20 can have a surface with a flaw 27, a discolored portion 28, a pinhole 29 and/or a similar defect. These defects are caused in a superconducting wire production process at a drawing step, a rolling step, a sintering step and/or the like. Herein, discolored portion 28 is a defect caused as a material contained in oxide superconductor filament 21 leaks out to sheath 22 and thus locally reduces sheath 22 in thickness, and when it is externally observed it appears to be discolored. Discolored portion 28 is a defect which tends to arise around pinhole 29.

In the present embodiment superconducting wire 20 is inspected with an inspection apparatus, as will be described hereinafter.

Figure 3:
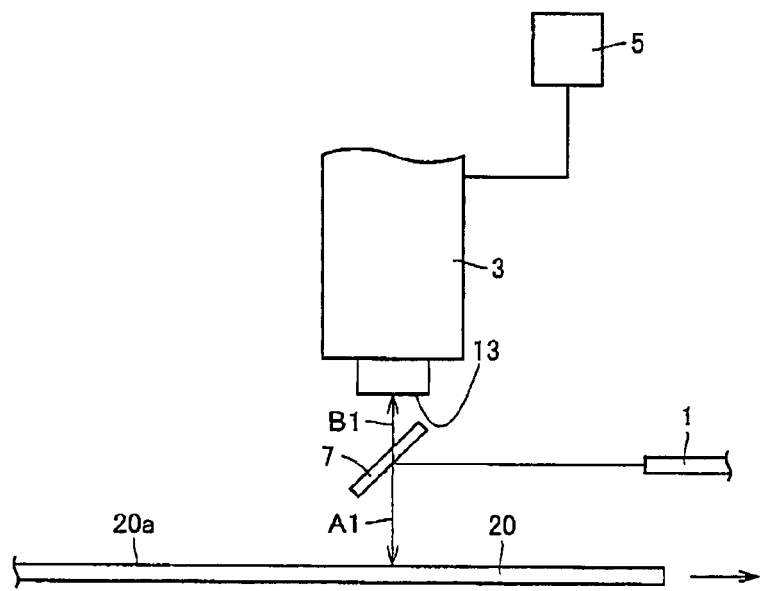
FIG. 3 schematically shows a configuration of the present superconducting wire inspection apparatus in a first embodiment.

FIG. 3 schematically shows a configuration of the present superconducting wire inspection apparatus provided in the first embodiment. With reference to FIG. 3 the present embodiment provides the superconducting wire inspection apparatus including a blue light emitting diode (blue LED) 1 serving as an illumination unit, a color line sensor 3 serving as a photoreceptive unit, a computer 5 serving as an output unit, and a mirror 7. Blue LED 1 and color line sensor 3 are arranged exactly, vertically over superconducting wire 20 at a predetermined position. Color line sensor 3 has a photoreceptive window 13 directed in a direction normal to a front surface 20a of superconducting wire 20. Mirror 7 is arranged between color line sensor 3 and superconducting wire 20. Computer 5 is electrically connected to color line sensor 3.

In the present embodiment superconducting wire 20 is inspected in a method as described hereinafter.

Blue LED 1 emits blue light to mirror 7 in a longitudinal direction of superconducting wire 20. Mirror 7 receives the light from blue LED 1 and reflects the light in the direction normal to front surface 20a of superconducting wire 20. Blue LED 1 thus serves as a coaxial illumination unit emitting light for illumination A1 in the direction normal to front surface 20a of superconducting wire 20.

If superconducting wire 20 does not have a defect, superconducting wire 20 receiving light for illumination A1 reflects the light in the same direction with an angle of reflection equal to that of incidence. In the present embodiment a reflection of light B1 is provided in the direction normal to front surface 20a. The reflection of light B1 is transmitted through mirror 7 and received by color line sensor 3.

Figure 4:
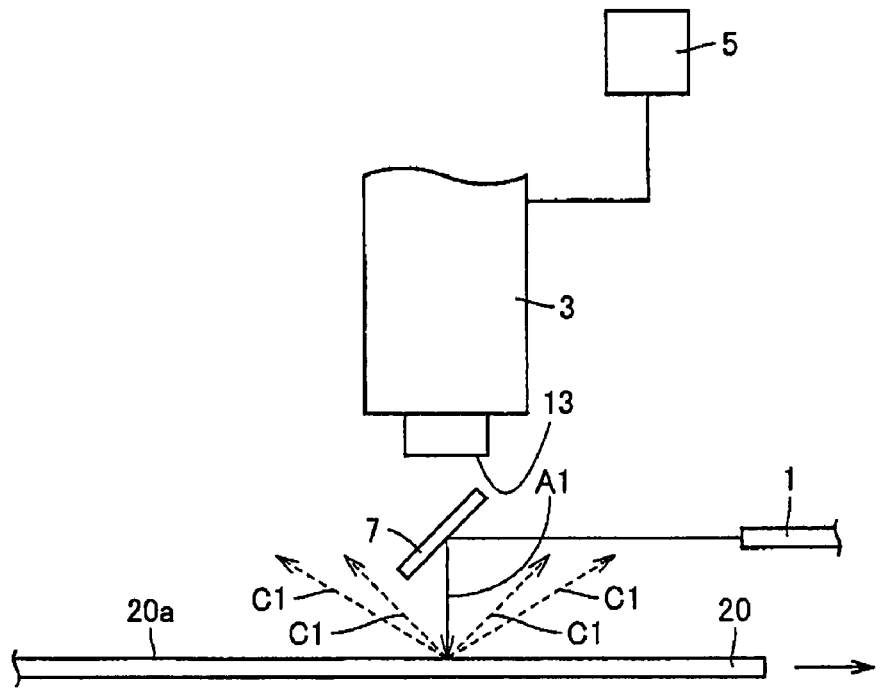
FIG. 4 schematically shows in which direction light travels when the present superconducting wire inspection apparatus in the first embodiment inspects a superconducting wire having a defect.

In contrast, with reference to FIG. 4, if superconducting wire 20 has a defect, then superconducting wire 20 receiving the light for illumination A1 diffuses the light on front surface 20a in various directions. This light is diffused light C1. Thus; if superconducting wire 20 has a defect, diffused light C1 is provided and color line sensor 3 receives light varying in quantity.

Herein in the present embodiment color line sensor 3 is arranged at a position to mainly receive the reflection of light B1. As such, if superconducting wire 20 has a defect, then color line sensor 3 receives only a portion of diffused light C1 and thus normally receives a decreased quantity of light. In other words, color line sensor 3 is a unit receiving a reflection of light, that mainly receives the reflection of light B1.

Color sensor 3 receives light and transmits its quantity data to computer 5, which accumulates the data and outputs cumulative data in quantity of light, and from the cumulative data, whether superconducting wire 20 has a defect or not is inspected. Hereinafter one example of the above described process performed in computer 5 will more specifically be described.

Figure 5:
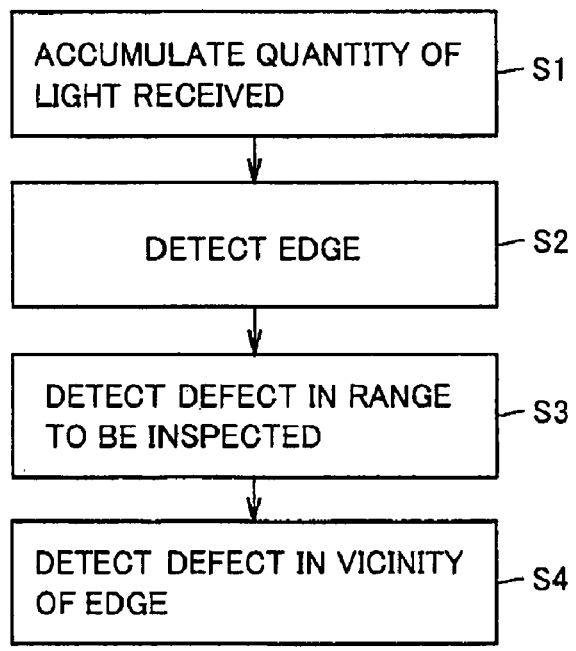
FIG. 5 is a flow chart of a process performed by a computer.
Figure 6:
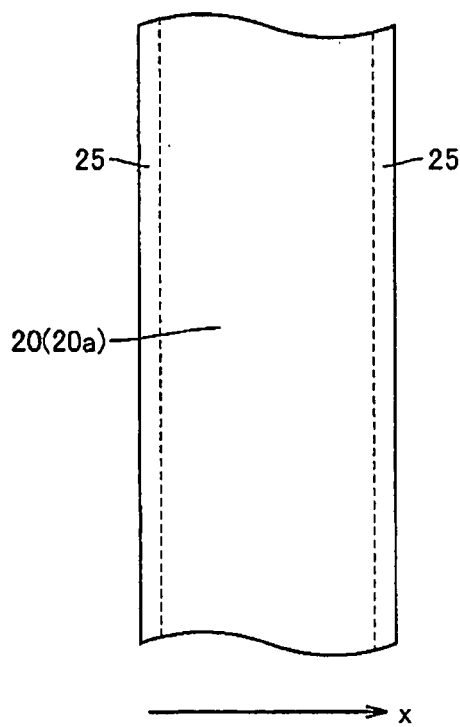
FIG. 6 is an enlarged view of a surface of a superconducting wire.

FIG. 5 is a flow chart of a process performed by the computer, as indicated in the order of the steps thereof FIG. 6 is an enlarged view of a surface of a superconducting wire. With reference to FIGS. 5 and 6, superconducting wire 20 has front surface 20a segmented widthwise (or in a direction x) by a width for example of approximately 10.0 μm and thus divided in 2,048 lines. Each line reflects light, which is received by color line sensor 3 and accumulated in quantity and thus output (step 1).

Figure 7:
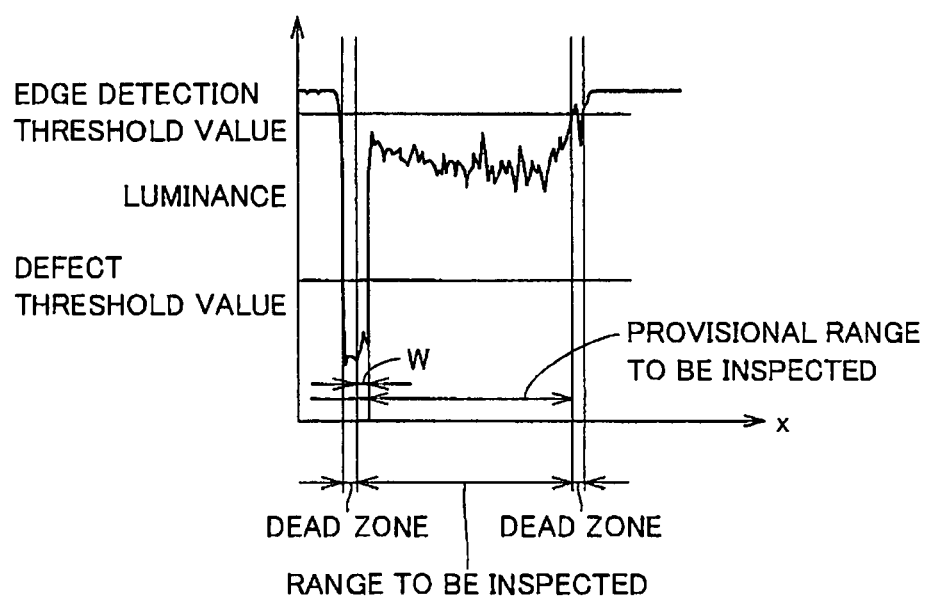
FIG. 7 represents one example of a distribution in luminance of cumulative light in a direction x.

FIG. 7 represents a distribution in luminance of such cumulative light in direction x. With reference to FIGS. 5-7, subsequently in accordance with the distribution in luminance of the cumulative light in direction x an edge 25 is detected (step S2). More specifically, if superconducting wire 20 is in the form of tape, front surface 20a has edge 25 having a curved surface, and color light sensor 3 receives a quantity of light significantly different from that reflected at a center of front surface 20a. Accordingly, edge 25 needs to be detected to prevent variation in quantity of light at edge 25 from erroneous recognition as a defect. More specifically, an edge detection threshold value is provided for the distribution in luminance of cumulative light in direction x and a range exceeding the edge detection threshold value is determined as an edge and set as a dead zone. In FIG. 7 the edge detection threshold value is exceeded at a portion located in the figure at right and left sides and indicated as a dead zone, and a range indicated by a width W. Accordingly in step S2 these two ranges are determined as an edge. Furthermore a range excluding the portion located in the figure at the right and left sides and indicated as a dead zone and the range indicated by width W, is determined as a provisional range to be inspected.

Subsequently for the provisional range to be inspected whether there is a defect or not is detected (a step S3). More specifically, a defect threshold value is provided for the distribution in luminance of the cumulative light in direction x, and if the provisional range to be inspected has a portion exceeding the defect threshold value, the portion is measured in width. If there is more than one portion exceeding the defect threshold value, the portions are individually measured in width, and any portion exceeding the defect threshold value that has a width equal to or larger than a prescribed width, is determined as a defect. In FIG. 7 the provisional range to be inspected does not have a portion exceeding the defect threshold value. Accordingly at step S3 no defect is detected.

Subsequently whether there is a defect in a vicinity of the edge is detected (step S4). More specifically, the provisional range to be inspected is compared with the actual superconducting wire in width and if the former is smaller than the latter in width by a value equal to or larger than a prescribed value, then a decision is made that there is a defect in the vicinity of the edge. In FIG. 7 the provisional range to be inspected is smaller than the actual superconducting wire in width by a value equal to or larger than the prescribed value. Accordingly the range indicated by width W is determined as a defect existing in the range to be inspected. By the above described method, whether superconducting wire 20 has front surface 20a with a defect or not is inspected.

In the superconducting wire inspection apparatus and method of the present embodiment, diffused light C1 reflected by superconducting wire 20 at flaw 27 in a surface, discolored portion 28, pinhole 29 and/or a similar defect and light B1 reflected by superconducting wire 20 at a defectless portion are reflected in different directions, respectively, whether the defect may be large or small. Accordingly color line sensor 3 receives light varying in quantity with whether there is defect or not, and from such variation in quantity of light, whether there is a defect or not is inspected. This allows even a small defect to be also detected, and superconducting wire 20 can be inspected for defects with high sensitivity. Furthermore, it can be inspected for defects faster than when it is visually done so.

In the present embodiment the inspection apparatus has color line sensor 3 serving as a photoreceptive unit receiving a reflection of light, that mainly receives light reflected B1 by superconducting wire 20.

In the inspection method of the present embodiment the light reflected B1 by superconducting wire 20 is mainly received.

Superconducting wire 20 provides the reflection of light B1, which varies in quantity of light with whether there is a defect or not, and in accordance with such variation in quantity of light, whether there is a defect or not can be inspected with high sensitivity.

In the present embodiment the inspection apparatus has blue LED 1 serving as a coaxial illumination unit emitting light in a direction normal to a surface of superconducting wire 20 to illuminate the surface.

In the present embodiment the inspection method includes emitting light in a direction normal to a surface of superconducting wire 20 to illuminate the surface.

This particularly helps to detect flaw 27 in the surface of superconducting wire 20.

While the present embodiment has been described with a computer processing indicated as an example, the present invention is not limited to such computer processing; it may be any process that at least accumulates a quantity of light received by a photoreceptive unit and thus outputs a cumulative quantity of light.

Furthermore, while the present embodiment has been described with an illumination unit implemented by a blue LED, the blue LED may be replaced with a red LED, or it may be implemented by an illumination unit emitting light having another wavelength.

Furthermore, blue LED 1 and color line sensor 3 may have any positional relationship that allows a photoreceptive unit to be arranged at a position to receive the reflection of light, and an effect similar to that of the present embodiment can be obtained. Furthermore, the photoreceptive unit may be arranged at any position that allows the photoreceptive unit to receive light at least from a superconducting wire.

Second Embodiment

Figure 8:
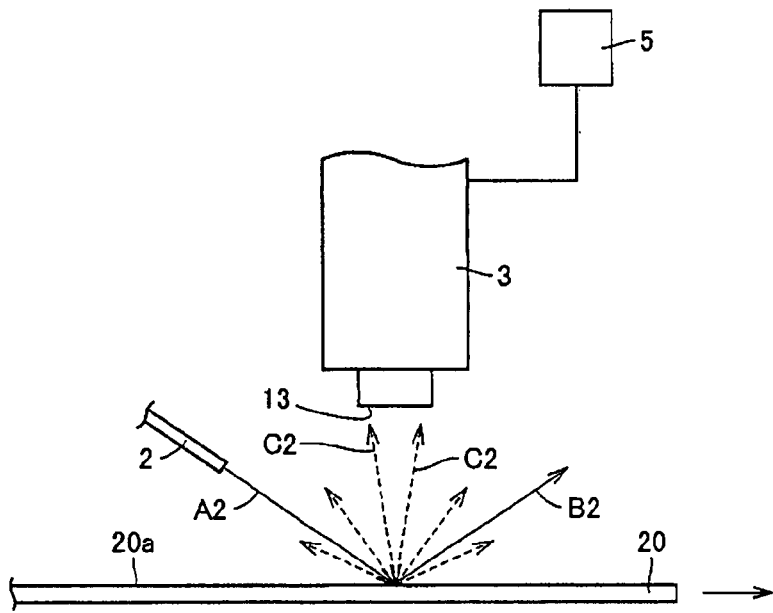
FIG. 8 schematically shows configuration of the superconducting wire inspection apparatus in second embodiment.

FIG. 8 schematically shows a configuration of the present superconducting wire fabrication apparatus provided in a second embodiment. With reference to FIG. 8 the present embodiment provide the superconducting wire inspection apparatus including an illumination unit implemented by a red LED 2 rather than a blue LED. Red LED 2 is arranged exactly, vertically over superconducting wire 20 at a predetermined position.

Color line sensor 3 is positioned and photoreceptive window 13 is directed, similarly as described in the first embodiment. More specifically, color line sensor 3 is arranged exactly, vertically over superconducting wire 20 at a predetermined position and its photoreceptive window 13 is directed in a direction normal to front surface 20a.

The remainder of the superconducting wire inspection apparatus in configuration is substantially similar to that of the first embodiment. Accordingly it will not be described repeatedly.

In the present embodiment a superconducting wire is inspected in a method, as will be described hereinafter.

Red LED 2 emits light for illumination A2 in a direction forming an angle with a direction normal to front surface 20a of superconducting wire 20. In other words, red LED 2 is an oblique illumination unit. If superconducting wire 20 is defectless, the light for illumination A2 emitted by red LED 2 to illuminate superconducting wire 20 is reflected with an angle of reflection equal to that of incidence. In the present embodiment a reflection of light B2 is provided, and color line sensor 3 receives the reflection of light B2 slightly.

If superconducting wire 20 has a defect, then front surface 20a provides diffused light C2 in various directions and a portion of diffused light C2 is received by color line sensor 3. Thus if superconducting wire 20 has a defect, diffused light C2 is caused and color line sensor 3 receives light varying in quantity.

Herein in the present embodiment color line sensor 3 is arranged at a position to mainly receive diffused light C2 (or less readily receive the reflection of light B2). Accordingly if superconducting wire 20 has a defect color line sensor 3 normally receives an increased quantity of light. In other words, color line sensor 3 serves as a photoreceptive unit receiving diffused light that mainly receives light diffused C2 by superconducting wire 20.

Color line sensor 3 receives light and transmits its quantity data to computer 5, which accumulates the data and thus outputs cumulative data in quantity of light. The cumulative data is used in a method similar to that of the first embodiment to inspect whether superconducting wire 20 has a defect or not.

In the present embodiment the inspection apparatus has color line sensor 3 serving as a photoreceptive unit receiving diffused light, that mainly receives light diffused C2 by superconducting wire 20.

In the inspection method of the present embodiment the light diffused C2 by superconducting wire 20 is mainly received.

Superconducting wire 20 provides diffused light, which varies in quantity of light with whether there is a defect or not, and in accordance with such variation in quantity of light, whether there is a defect or not can be inspected.

Furthermore, read LED 2 and color line sensor 3 may have any positional relationship that allows a photoreceptive unit to be arranged at a position to receive the diffused light, and an effect similar to that of the present embodiment can be obtained.

Third Embodiment

Figure 9:
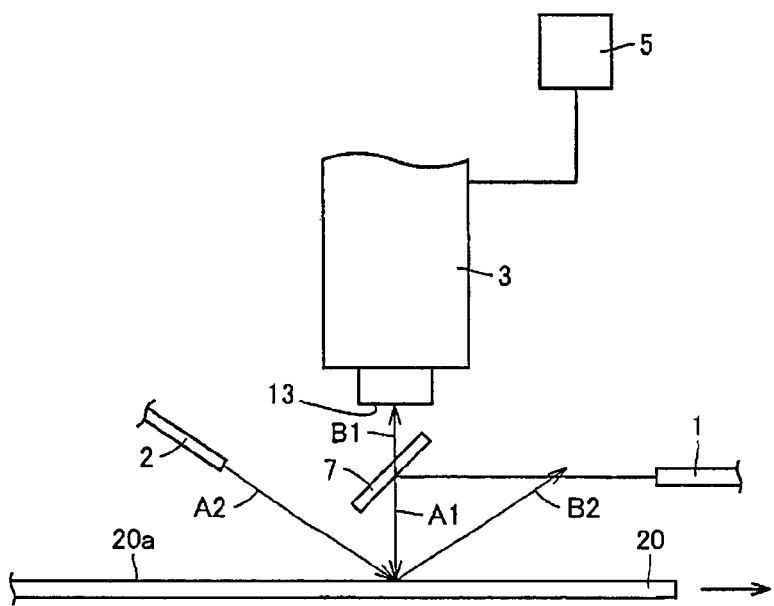
FIG. 9 schematically shows configuration of the superconducting wire inspection apparatus in third embodiment.

FIG. 9 schematically shows a configuration of the present the superconducting wire inspection apparatus provided in a third embodiment. With reference to FIG. 9 the present embodiment provides the superconducting wire inspection apparatus including blue LED 1 serving as a coaxial illumination unit, red LED 2 serving as an oblique illumination unit, color line sensor 3 serving as a photoreceptive unit receiving a reflection of light and a photoreceptive unit receiving diffused light, computer 5 serving as an output unit, and mirror 7. Blue LED 1, red LED 2, and color line sensor 3 are arranged exactly, vertically over superconducting wire 20 at predetermined positions, respectively. Color line sensor 3 has photoreceptive window 13 directed in a direction normal to front surface 20a of superconducting wire 20.

The remainder of the superconducting wire inspection apparatus in configuration is substantially similar to that of the first embodiment. Accordingly it will not be described repeatedly.

In the present embodiment a superconducting wire is inspected in a method, as will be described hereinafter.

Blue LED 1 emits light for illumination A1 in a direction normal to front surface 20a of superconducting wire 20 in a method similar to that described in the first embodiment. Red LED 2 emits light for illumination A2 in a direction forming an angle with the direction normal to front surface 20a of superconducting wire 20.

If superconducting wire 20 is defectless, the blue light for illumination A1 and the red light for illumination A2 illuminating superconducting wire 20 are each reflected in the same direction with an angle of reflection equal to that of incidence. In the present embodiment a reflection of the blue light B1 is provided in the direction normal to front surface 20a and a reflection of the red light B2 is provided in a direction forming an angle with front surface 20a. Of these reflections, that of the blue light B1 is transmitted through mirror 7 and received by color line sensor 3. Furthermore, color line sensor 3 receives the reflection of the red light B2 slightly.

Figure 10:
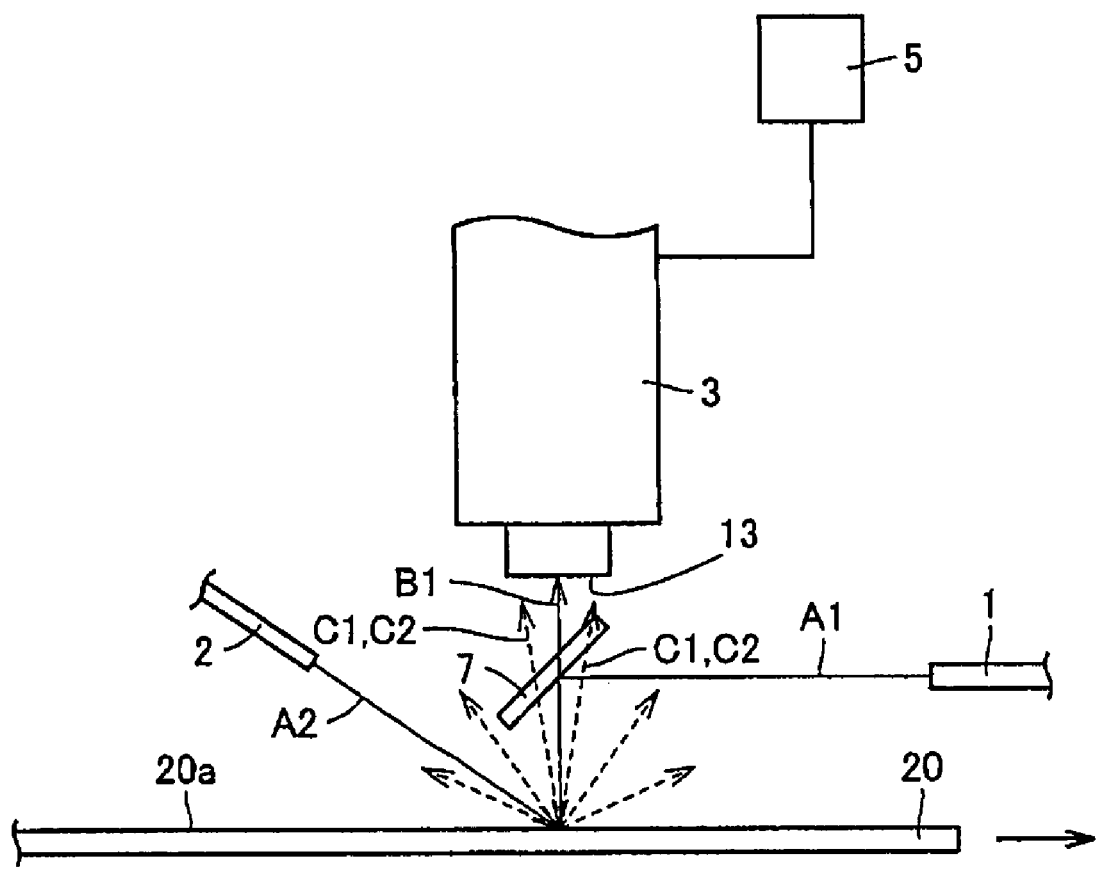
FIG. 10 schematically shows in which direction light travels when the present superconducting wire inspection apparatus in the third embodiment inspects a superconducting wire having a defect.

In contrast, with reference to FIG. 10, if superconducting wire 20 has a defect, then the light for illumination A1 and that for illumination A2 illuminating superconducting wire 20 are each diffused by front surface 20a in various directions and thus provide diffused light C1, C2, and a portion of diffused light C1, C2 is received by color line sensor 3. Thus if superconducting wire 20 has a defect, diffused light C1, C2 is caused and color line sensor 3 receives blue light and red light each varying in quantity.

Herein in the present embodiment color line sensor 3 is arranged at a position to mainly receive the reflection of light B1 as compared with diffused light C1. Accordingly, if superconducting wire 20 has a defect, color line sensor 3 receives a decreased quantity of the blue light. In other words, color line sensor 3 serves as a photoreceptive unit receiving a reflection of light, that mainly receives the reflection of light B1.

Furthermore in the present embodiment color line sensor 3 is arranged at a position to mainly receive diffused light C2 as compared with the reflection of light B2. Accordingly, if superconducting wire 20 has a defect, color line sensor 3 receives a decreased quantity of the red light. In other words, color line sensor 3 serves as a photoreceptive unit receiving diffused light, that mainly receives diffused light C2.

Color line sensor 3 receives light and transmits its quantity data to computer 5, which follows a method similar to that of the first embodiment to accumulate the data and thus output cumulative data in quantity of light. From the cumulative data, whether superconducting wire 20 has a defect or not is inspected.

In the present embodiment blue LED 1 generates light having a wavelength and red LED 2 generates light having a different wavelength. Accordingly if color line sensor 3 receives both blue light and red light, computer 5 can divide the lights having the different wavelength, respectively, and thus analyze them, and accumulate their quantities separately and output them separately. Color line sensor 3 can thus fulfill both the function of a photoreceptive unit receiving a reflection of light and that of a photoreceptive unit receiving diffused light. It is a matter of course that a photoreceptive unit receiving a reflection of light for receiving blue light and that receiving diffused light for receiving red light may separately be provided.

The present embodiment thus provides a superconducting wire inspection apparatus including color line sensor 3 receiving the reflection of light B1 and diffused light C2 to more readily detect variation in quantity of light than when only a single light is received. This allows a defect to be detected with good precision. Furthermore the illumination unit including both blue and red LEDs 1 and 2 can help to detect both a flaw in a surface of a superconducting wire and a pinhole of the superconducting wire.

Fourth Embodiment

Figure 11:
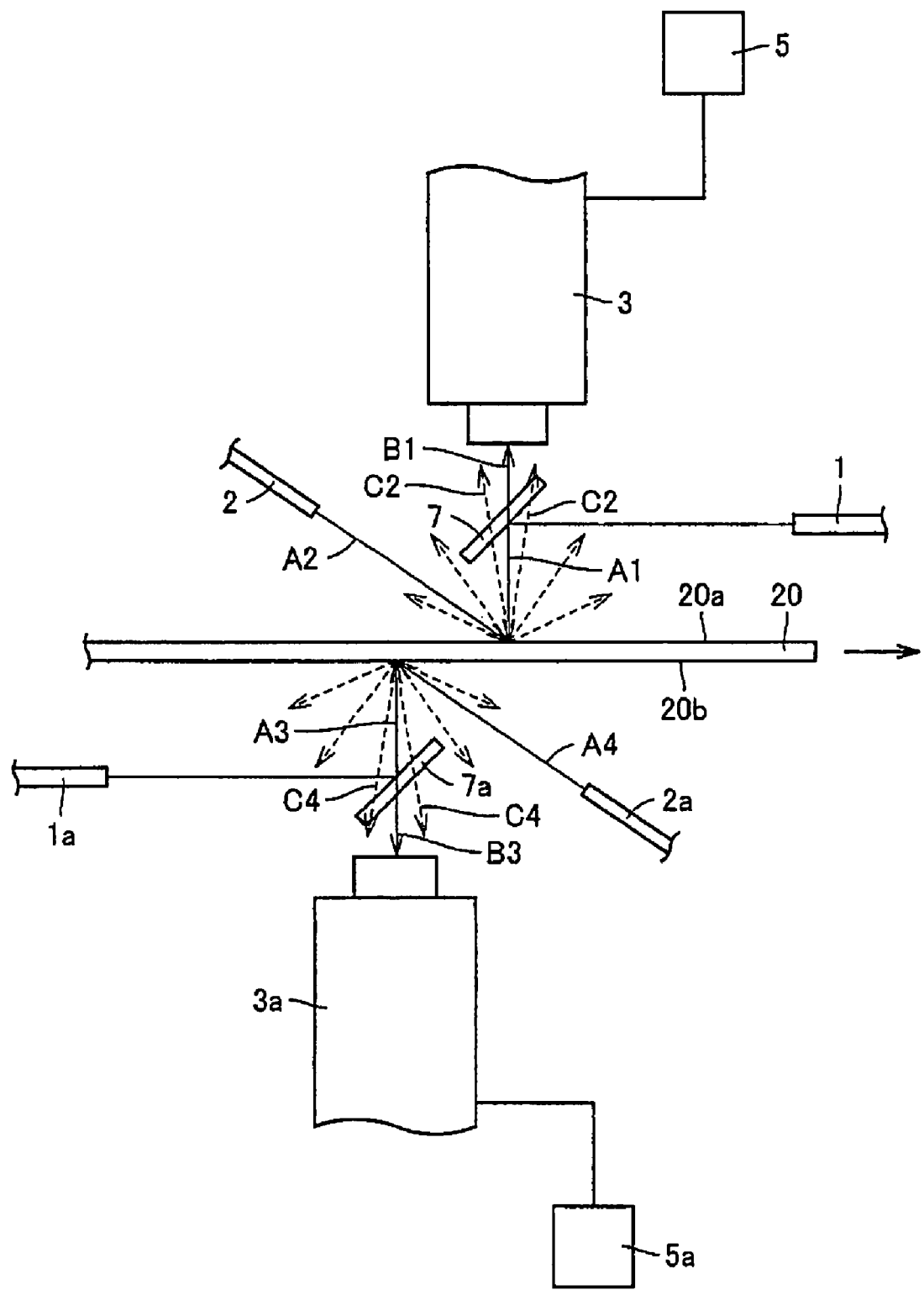
FIG. 11 schematically shows a configuration of the present superconducting wire inspection apparatus in a fourth embodiment.

FIG. 11 schematically shows a configuration of the present superconducting wire inspection apparatus in a fourth embodiment. With reference to FIG. 11 the present embodiment provides the superconducting wire inspection apparatus including two inspection apparatuses similar in configuration to that of the third embodiment and arranged at positions facing superconducting wire 20 at front surface 20*a* and a back surface 20*b*, respectively.

The inspection apparatus facing superconducting wire 20 at front surface 20*a* includes blue LED 1, red LED 2, color line sensor 3, computer 5 and mirror 7. Blue LED 1 emits blue light for illumination A1 to illuminate the superconducting wire at front surface 20*a* and mainly the reflection of light B1 of the blue light is received by color line sensor 3. Furthermore, red LED 2 emits red light for illumination A2 to illuminate the superconducting wire at front surface 20*a* and mainly, diffused light C2 of the red light is received by color line sensor 3.

Furthermore, the inspection apparatus facing superconducting wire 20 at back surface 20*b* includes a blue LED 1*a*, a red LED 2*a*, a color line sensor 3*a*, a computer 5*a* and a mirror 7*a*. Blue LED 1*a* emits blue light for illumination A3 to illuminate the superconducting wire at back surface 20*b* and mainly a reflection of light B3 of the blue light is received by color line sensor 3. Furthermore, red LED 2*a* emits red light for illumination A4 to illuminate the superconducting wire at back surface 20*b* and mainly, diffused light C4 of the red light is received by color line sensor 3.

Note that the present embodiment provides the two inspection apparatuses similar in configuration to that of the third embodiment, and the two inspection apparatuses each inspect a superconducting wire in a method similar to that described in the third embodiment. Accordingly they will not be described repeatedly.

If the superconducting wire inspection apparatus of the present embodiment inspects superconducting wire 20 is in the form of tape, it can inspect front surface 20*a* and back surface 20*b* simultaneously and thus inspect the wire more efficiently.

Note that while the present embodiment provides two inspection apparatuses, the present invention may include three or more inspection apparatuses. An increased number of inspection apparatuses for example allows a round superconducting wire or the like to have its circumferential surface inspected all at a time.

Furthermore, while the present embodiment includes two inspection apparatuses each corresponding to that of the third embodiment, the present embodiment may alternatively include two inspection apparatuses each corresponding to that of the first or second embodiment.

Fifth Embodiment

Figure 12:
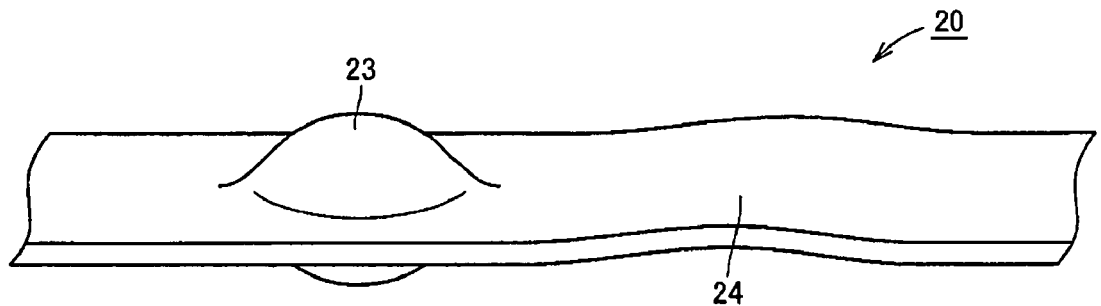
FIG. 12 schematically shows blister or a similar defect caused in a superconducting wire.

The first to fourth embodiments indicate an inspection apparatus (hereinafter also referred to as an optical inspection apparatus) particularly suitable for detecting a defect such as pinhole 29 shown in FIG. 2. However, in addition to such pinhole or a similar defect, superconducting wire 20 can also blister 23, bend 24 and/or have a similar defect, as shown in FIG. 12, and/or have local variation in width, deformation, deflection, waviness, swelling and/or a similar defect. These defects are caused in a superconducting wire fabrication process at a drawing step, a rolling step, a sintering step and/or the like. In particular, the superconducting wire blisters 23 when a matter attracted and thus adhering to a powdery source material of superconducting wire 20 evaporates in the sintering step and thus increases in volume. Accordingly in the following, fifth to eight embodiments will be described an inspection apparatus and method capable of inspecting blister, bending, local variation in width, deformation, deflection, waviness, swelling and similar defects in particular with high sensitivity. These defects are accompanied with deformation larger than a pinhole or a similar defect are.

Figure 13:
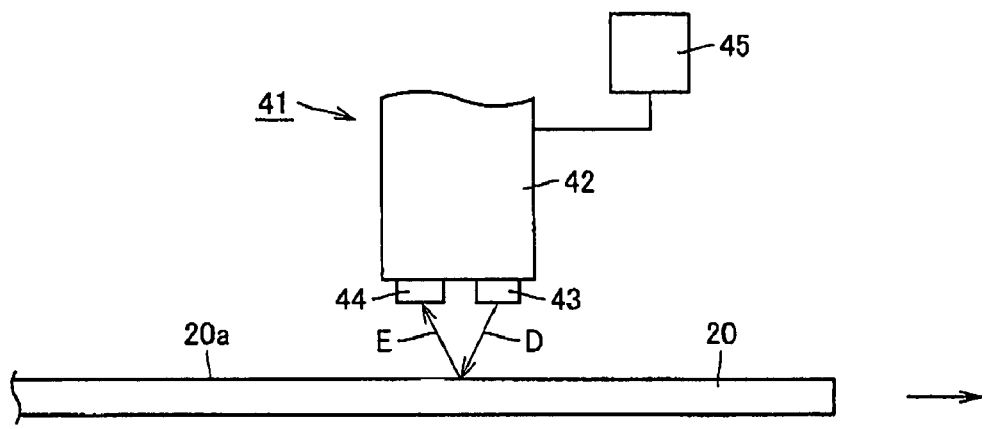
FIG. 13 schematically shows a configuration of the present superconducting wire inspection apparatus in a fifth embodiment.

FIG. 13 schematically shows a configuration of the superconducting wire inspection apparatus in the fifth embodiment. With reference to FIG. 13, the present embodiment provides the superconducting wire inspection apparatus including the optical inspection apparatus indicated in any of the first to fourth embodiments plus a laser displacement sensor 41 including a semiconductor laser serving as a laser light illumination unit, an optical position sensitive device (PSD) 44 serving as a laser light receiving unit, and a computer 45 serving as an output unit for the laser displacement sensor. Semiconductor laser 43 and PSD 44 are mounted on a sensor head 42 at an end, and sensor head 42 is arranged over front surface 20*a* of superconducting wire 20. Semiconductor laser 43 and PSD 44 are electrically connected via sensor head 42 to computer 45.

When laser displacement sensor 41 is employed, superconducting wire 20 is inspected in a method as will be described hereinafter.

While semiconductor laser 43 emits a laser beam of light D to illuminate superconducting wire 20, semiconductor laser 43 is also moved relative to superconducting wire 20 in the longitudinal direction of superconducting wire 20. In FIG. 13 semiconductor laser 43 is fixed and superconducting wire 20 is moved rightward as seen in the figure. Superconducting wire 20 is thus exposed to the laser beam of light D in the longitudinal direction of the wire. The laser beam of light D is reflected by superconducting wire 20 at front surface 20*a* and a laser beam of light E is received by PSD 44.

Figure 14:
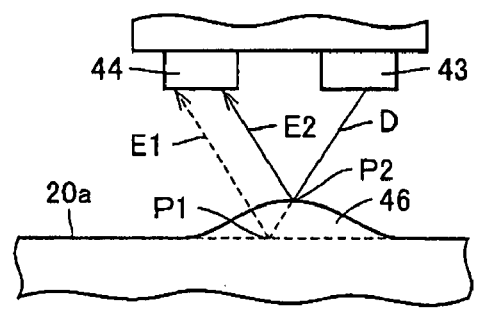
FIG. 14 shows in the fifth embodiment how a position receiving light varies with whether a superconducting wire has a surface displaced in the direction of the thickness of thereof.

Herein, with reference to FIG. 14, if superconducting wire 20 does not have front surface 20*a* displaced in the direction of the thickness thereof (or the wire is defectless), the laser beam of light D is reflected at a position P1 and the laser beam of light E1 is received by PSD 44. In contrast, if superconducting wire 20 has blister 46 or a similar defect and thus has front surface 20*a* displaced in the direction of the thickness thereof, then the laser beam of light D is reflected at a position P2 and a laser beam of light E2 is received by PSD 44. In other words, PSD 44 receives the laser beam of light E at a position varying with how front surface 20*a* of superconducting wire 20 is displaced and whether there is a defect or not, the defect's size and geometry.

PSD 44 transmits to computer 45 the data of a position at which the laser beam of light E is received. Computer 45 uses the data and employs triangulation to calculate a position of front surface 20*a* of superconducting wire 20 (i.e., a position at which the laser beam of light D is reflected) and output information on how front surface 20*a* of superconducting wire 20 is displaced. As a result, whether superconducting wire has front surface 20*a* with a defect or not is detected.

In the present embodiment the apparatus inspecting superconducting wire 20 further includes laser displacement sensor 41 having semiconductor laser 43 moving relative to superconducting wire 20 in the longitudinal direction of superconducting wire 20 while emitting the laser beam of light D to illuminate front surface 20a of superconducting wire 20, PSD 44 receiving the laser beam of light E reflected by superconducting wire 20, and computer 45 outputting information on displacement of superconducting wire 20 as based on a position on PSD 44 at which it receives light.

In the present embodiment superconducting wire 20 is inspected in a method including the steps of: emitting the laser beam of light D to illuminate superconducting wire 20 in the longitudinal direction thereof; receiving the laser beam of light E reflected by superconducting wire 20 on front surface 20a; and outputting information on displacement of superconducting wire 20 as based on a position at which the laser beam of light E is received.

In the present embodiment the apparatus and method of inspecting superconducting wire 20 can provide information on how front surface 20a of superconducting wire 20 is displaced. This allows bulging, bending, local variation in width, deformation and other similar defects to be inspected with high sensitivity. Furthermore, it also allows a defect to be numerically measured, and not only whether there is a defect or not but also the defect's size, geometry and the like to be also measured. As a result, the superconducting wire can be inspected more effectively.

It should be noted that the optical inspection apparatus and the laser displacement sensor may be used, as described hereinafter, to inspect superconducting wire 20. For example, the optical inspection apparatus may inspect which portion has a defect, and transmit information of its location to the laser displacement sensor, and the laser displacement sensor may measure the defect in size, geometry and the like. Furthermore, for example, the laser displacement sensor may inspect whether bending or a similar, large defect is present or absent and the optical inspection apparatus may inspect whether there is a pinhole or a similar small defect. Thus adjusting the optical inspection apparatus and the laser displacement sensor each in sensitivity depending on application allows the computer to process a signal in a reduced period of time and an inspection to be contacted more efficiently.

Furthermore in the present embodiment the function as computer 45 may be fulfilled by computer 5 (FIG. 3). In that case, semiconductor laser 43 and PSD 44 are electrically connected to computer 5. This allows a single computer to be used to conduct an inspection.

Figure 15:
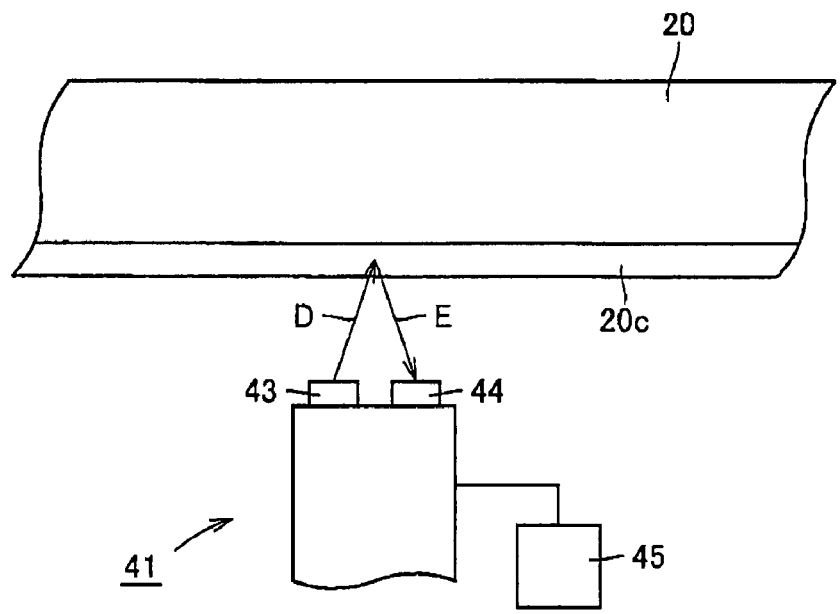
FIG. 15 is a diagram for illustrating employing the present superconducting wire inspection apparatus of the fifth embodiment to measure how an end surface of a superconducting wire is displaced.

Furthermore, rather than illuminating superconducting wire 20 at front surface 20a, the laser beam of light D may illuminate superconducting wire 20 at an end surface 20c, as shown in FIG. 15. How end surface 20c of superconducting wire 20 is displaced can thus be measured and superconducting wire 20 can thus be inspected in width.

Sixth Embodiment

Figure 16:
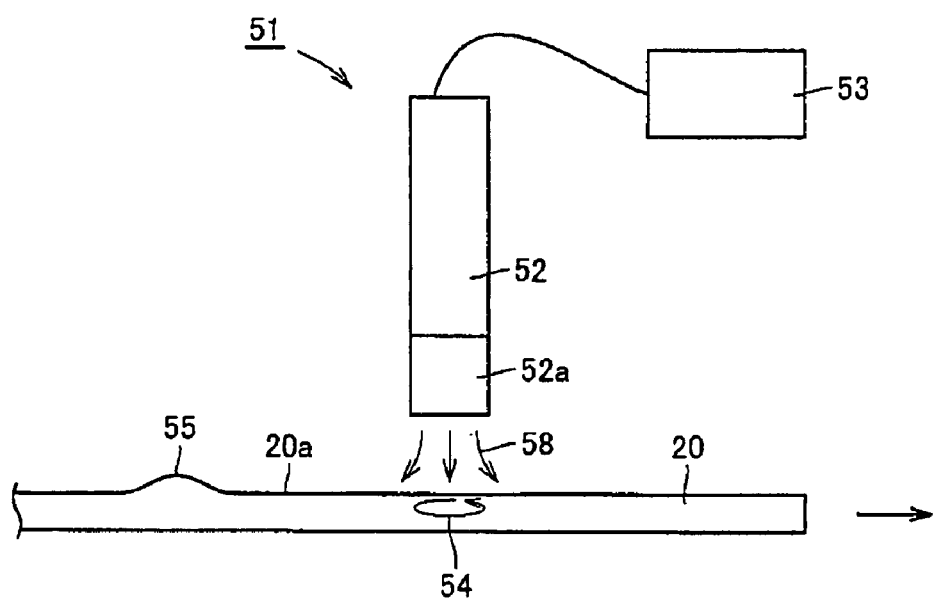
FIG. 16 schematically shows a configuration of the present superconducting wire inspection apparatus in a sixth embodiment.

FIG. 16 schematically shows a configuration of the present superconducting wire inspection apparatus in a sixth embodiment. With reference to FIG. 16, the present embodiment provides the superconducting wire inspection apparatus including the optical inspection apparatus indicated in any of the first to fourth embodiments plus an eddy current displacement sensor 51 including a main body 53 serving as an alternate current generation unit and an output unit for the eddy current displacement sensor, and a coil 52a serving as a coil for the eddy current displacement sensor. A probe 52 is arranged adjacent to superconducting wire 20 over front surface 20a, and coil 52a is attached to an end of probe 52. Coil 52a is electrically connected via probe 52 to main body 53.

When eddy current displacement sensor 51 is employed, superconducting wire 20 is inspected in a method as will be described hereinafter.

When main body 53 applies an alternate current voltage to coil 52a, coil 52a has an alternate current flowing therethrough and generates a magnetic field 58 varying periodically. As magnetic field 58 thus varies, an eddy current 54 is generated at front surface 20a of superconducting wire 20. While probe 52 generates eddy current 54 at front surface 20a of superconducting wire 20, probe 52 is moved relative to superconducting wire 20 in a longitudinal direction of superconducting wire 20. In FIG. 16, probe 52 is fixed and superconducting wire 20 is moved rightward as seen in the figure. This generates eddy current 54 at front surface 20a of superconducting wire 20 in the longitudinal direction of superconducting wire 20. Eddy current 54 affects how coil 52a oscillates. More specifically, it varies from an oscillating waveform serving as a reference (i.e., an oscillating waveform in a condition which is not affected by eddy current).

Figure 17:
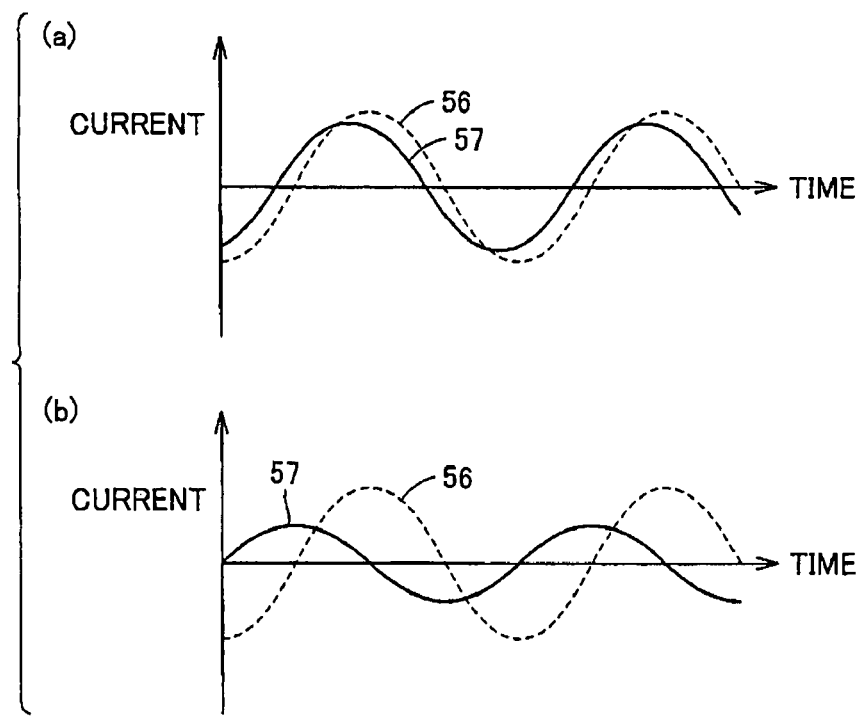
FIG. 17(a) represents in waveform how a coil oscillates when a superconducting wire does not have a surface displaced in the direction of the thickness of thereof.
FIG. 17(b) represents in waveform how a coil oscillates when a superconducting wire has a surface displaced in the direction of the thickness of thereof.

Herein if superconducting wire 20 does not have front surface 20a displaced in the direction of the thickness thereof (i.e., the wire is defectless), coil 52a has a large distance to front surface 20a of superconducting wire 20 and is thus less affected by eddy current 54. Accordingly, coil 52a oscillates in a state with a small variation as shown in FIG. 17(a). In FIG. 17(a) the coil oscillates in a waveform 57 slightly varying from an oscillating waveform 56 serving as a reference. More specifically, oscillating waveform 57 is slightly smaller in amplitude than oscillating waveform 56 and slightly out of phase with oscillating waveform 56. In contrast, if superconducting wire 20 has blister 55 or a similar defect and thus has front surface 20a displaced in the direction of the thickness thereof then coil 52a has a small distance to front surface 20a of superconducting wire 20 and is thus increasingly affected by eddy current 54. Accordingly, coil 52a oscillates in a state with a large variation as shown in FIG. 17(b). More specifically, oscillating waveform 57 is significantly smaller in amplitude than oscillating waveform 56 and significantly out of phase with oscillating waveform 56. In other words, the degree of the variation of the state in which coil 52a oscillates varies with how front surface 20a of superconducting wire 20 is displaced and whether there is a defect or not and the defect's size, geometry and the like.

As eddy current 54 is generated, how coil 52a oscillates varies, and from such variation, main body 53 calculates the position of front surface 20a of superconducting wire 20 and outputs information on how front surface 20a of superconducting wire 20 is displaced. As a result, whether superconducting wire 20 has front surface 20a with a defect or not is detected.

The present embodiment provides the apparatus inspecting superconducting wire 20 further including eddy current displacement sensor 51 having main body 53 passing an alternate current through coil 52a, coil 52a moving relative to superconducting wire 20 in the longitudinal direction of superconducting wire 20 while generating eddy current 54 at superconducting wire 20, and main body 53 outputting information on displacement of superconducting wire 20 as based on such variation in how coil 52a oscillates that is caused as eddy current 54 is generated.

In the present embodiment superconducting wire 20 is inspected in a method further including the steps of: employing coil 52a with an alternate current passing therethrough to generate eddy current 54 at superconducting wire 20 in the longitudinal direction of superconducting wire 20; and outputting information of displacement of superconducting wire 20 as based on such variation in how coil 52a oscillates that is caused as eddy current 54 is generated.

The apparatus and method of inspecting superconducting wire 20 in the present embodiment can provide information on how front surface 20a of superconducting wire 20 is displaced. This allows bulging, bending, local variation in width, deformation and other similar defects in particular to be inspected with high sensitivity. Furthermore, it also allows a defect to be numerically measured, and not only whether there is a defect or not but also the defect's size, geometry and the like to be also measured. As a result, the superconducting wire can be inspected more effectively.

Furthermore, superconducting wire 20 having displacement widthwise (or in a direction perpendicular to the plane of the drawing of FIG. 16) also varies how eddy current 54 is generated, and how coil 52a oscillates accordingly varies. Eddy current displacement sensor 51 thus allows variation in the direction of the thickness of superconducting wire 20 but also that in the direction of the width thereof to be also measured.

Note that while in the present embodiment the alternate current generation unit passing an alternate current through coil 52a and the output unit associated with the eddy current displacement sensor and outputting information on displacement of superconducting wire 20 as based on such variation in how coil 52a oscillates that is caused as eddy current 54 is generated are both main body 53, the alternate current generation unit and the output unit associated with the eddy current displacement sensor may separately be configured. Furthermore while in the present embodiment how coil 52a varies in both amplitude and phase is used to calculate the position of front surface 20a of superconducting wire 20, how coil 52a varies in one of amplitude and phase may be used to calculate the position of front surface 20a of superconducting wire 20.

Furthermore the optical inspection apparatus and the eddy current displacement sensor may be used, as described hereinafter, to inspect superconducting wire 20. For example, the optical inspection apparatus may inspect which portion has a defect, and transmit information of its location to the eddy current displacement sensor, and the eddy current displacement sensor may measure the defect in size, geometry and the like. Furthermore, for example, the eddy current displacement sensor may inspect whether bending or a similar, large defect is present or absent and the optical inspection apparatus may inspect whether there is a pinhole or a similar small defect. Thus adjusting the optical inspection apparatus and the eddy current displacement sensor each in sensitivity depending on application allows the computer to process a signal in a reduced period of time and an inspection to thus be conducted more efficiently.

Furthermore in the present embodiment the function as the output unit associated with the eddy current displacement sensor may be fulfilled by computer 5 (FIG. 3). In that case, coil 52a is electrically connected to computer 5. This allows a single computer to be used to conduct an inspection.

Seventh Embodiment

Figure 18:
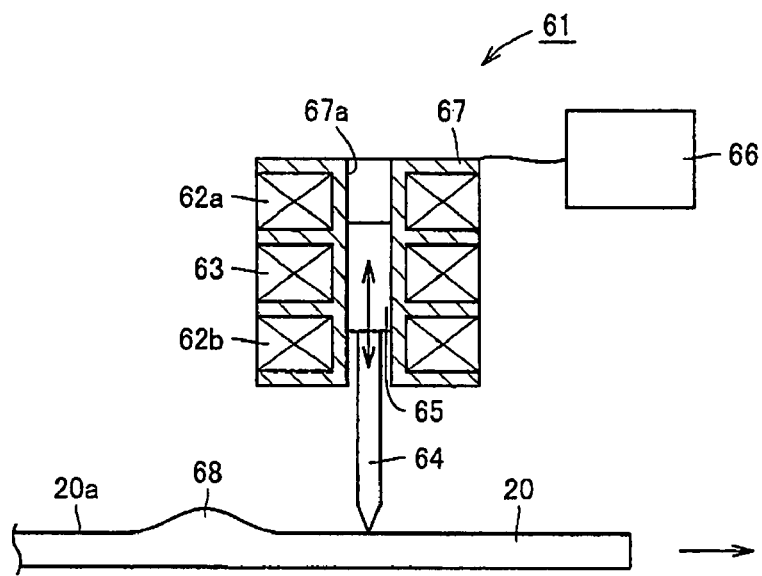
FIG. 18 schematically shows a configuration of the present superconducting wire inspection apparatus in a seventh embodiment.

FIG. 18 schematically shows a configuration of the present superconducting wire inspection apparatus in a seventh embodiment. With reference to FIG. 18, the present embodiment provides the superconducting wire inspection apparatus including the optical inspection apparatus indicated in any of the first to fourth embodiments plus a contact displacement sensor 61 having a probe 54, an iron core 65, a primary coil 63, two secondary coils 62a and 62b serving as a coil for the contact displacement sensor, a main body 66 serving as an output unit for the contact displacement sensor, and a casing 67. Probe 64 is arranged to have a tip to contact superconducting wire 20 on front surface 20a and has an upper portion with iron core 65 attached thereto. Casing 67 has a cylindrical geometry having a hollow portion 67a. The upper portion of probe 64 and iron core 65 are arranged in hollow portion 67a and slidable therein upward and downward as seen in the figure. Casing 67 has wound therearound secondary coil 62a, primary coil 63 underlying secondary coil 62a, and secondary coil 62b underlying primary coil 63. Primary coil 63 and secondary coils 62a and 62b are each electrically connected to man body 66.

Figure 19:
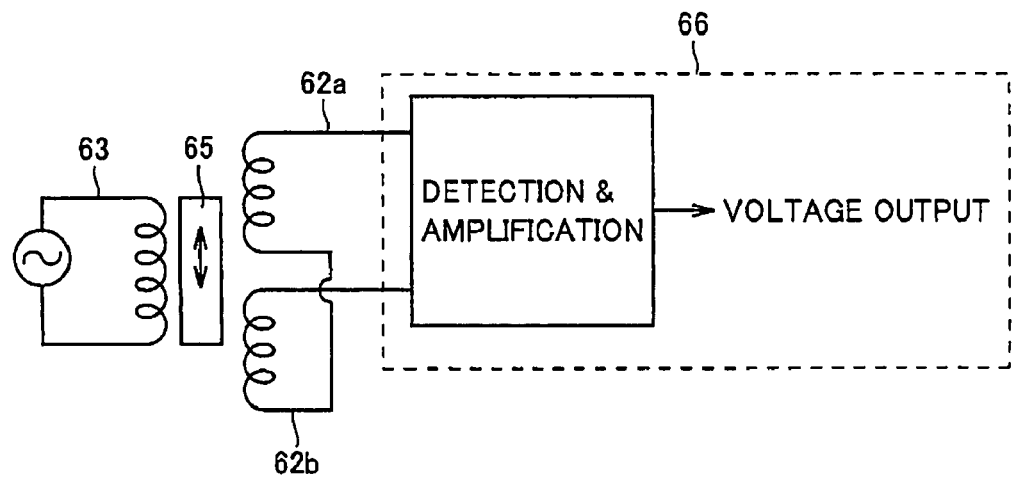
FIG. 19 is a circuit diagram of a contact displacement sensor shown in FIG. 18.

FIG. 19 is a circuit diagram of the contact displacement sensor shown in FIG. 18. With reference to FIG. 19, when primary coil 63 is excited by an alternate current voltage having a constant frequency, iron core 65 allows an alternate-current induced voltage to be generated at each of secondary coils 62a and 62b. The induced voltage generated at each of secondary coils 62a and 62b varies with the position of iron core 65 in upward and downward directions. Main body 66 detects a difference between the two induced voltages (an alternate current voltage) and amplifies the difference, and converts the amplified difference to direct current voltage. In other words, contact displacement sensor 61 utilizes a principle of a differential transformer.

When contact displacement sensor 61 is employed, superconducting wire 20 is inspected in a method as will be described hereinafter.

With reference to FIGS. 18 and 19, probe 64 is moved relative to superconducting wire 20 in the longitudinal direction of superconducting wire 20 in contact with superconducting wire 20 on front surface 20a. In FIG. 18 probe 64 is fixed and superconducting wire 20 is moved rightward as seen in FIG. 18.

Herein if superconducting wire 20 does not have front surface 20a displaced in the direction of the thickness thereof (or is defectless), iron core 65 is located at a position intermediate between secondary coils 62a and 62b, and at secondary coils 62a and 62b, induced voltages, respectively, equal in magnitude are generated. As a result, main body 66 obtains a direct current voltage of 0V. In contrast, if superconducting wire 68 has blister 68 or a similar defect and thus has front surface 20a displaced in the direction of the thickness thereof, then probe 64 and iron core 65 move in accordance with how front surface 20a is displaced, and thus slide in upward and downward directions as seen in FIGS. 18 and 19. If probe 64 slides upward, iron core 65 moves toward secondary coil 62a, and at secondary coil 62a an induced voltage larger than that of secondary coil 62b is generated. As a result, main body 66 obtains a direct current voltage having a positive value. If probe 64 slides downward, then iron core 65 moves toward secondary coil 62b, and at secondary coil 62b an induced voltage larger than that of secondary coil 62a is generated. As a result, main body 66 obtains a direct current voltage having a negative value. The more significantly probe 64 is displaced, the larger in magnitude main body 66 obtains a direct current voltage.

Main body 66 outputs information on how front surface 20a of superconducting wire 20 is displaced as based on whether the direct current is positive or negative and its magnitude. As a result, whether superconducting wire 20 has front surface 20a with a defect or not is detected.

The present embodiment provides an apparatus inspecting superconducting wire 20, including contact displacement sensor 61 having probe 64 moving relative to superconducting wire 20 in the longitudinal direction of superconducting wire 20 in contact with superconducting wire 20 and also moving in accordance with displacement of superconducting wire 20, iron core 65 attached to probe 64, secondary coils 62a and 62b generating induced electromotive force as iron core 65 moves, and main body 66 outputting information on displacement of superconducting wire 20 as based on the induced electromotive force.

In the present embodiment superconducting wire 20 is inspected in a method including the steps of: moving probe 64, having iron core 65 attached thereto, relative to superconducting wire 20 in the longitudinal direction of superconducting wire 20 in contact with superconducting wire 20; interlocking probe 64 with superconducting wire 20; and generating induced electromotive force at secondary coil 62a, 62b as iron core 65 moves, and outputting information on displacement of superconducting wire 20 as based on the induced electromotive force.

In the present embodiment the apparatus and method of inspecting superconducting wire 20 can provide information on how front surface 20a of superconducting wire 20 is displaced. This allows bulging, bending, local variation in width, deformation and other similar defects to be inspected with high sensitivity. Furthermore, it also allows a defect to be numerically measured, and not only whether there is a defect or not but also the defect's size, geometry and the like to be also measured. As a result, the superconducting wire can be inspected more effectively.

While the present embodiment has been described with a contact displacement sensor having a circuit as shown in FIG. 19, the contact displacement sensor of the present invention is not limited to that having such circuit, and may be any such displacement sensor that outputs information on displacement of superconducting wire 20 as based on electromotive force generated at a coil.

Furthermore the optical inspection apparatus and the contact displacement sensor may be used, as described hereinafter, to inspect superconducting wire 20. For example, the optical inspection apparatus may inspect which portion has a defect, and transmit information of its location to the contact displacement sensor, and the contact displacement sensor may measure the defect in size, geometry and the like. Furthermore, for example, the contact displacement sensor may inspect whether bending or a similar, large defect is present or absent and the optical inspection apparatus may inspect whether there is a pinhole or a similar small defect. Thus adjusting the optical inspection apparatus and the contact displacement sensor each in sensitivity depending on application allows the computer to process a signal in a reduced period of time and an inspection to thus be conducted more efficiently.

Furthermore in the present embodiment the function as main body 66 may be fulfilled by computer 5 (FIG. 3). In that case, primary coil 63 and secondary coils 62a narrowed down 62b are each electrically connected to computer 5. This allows a single computer to be used to conduct an inspection.

Eighth Embodiment

Figure 20:
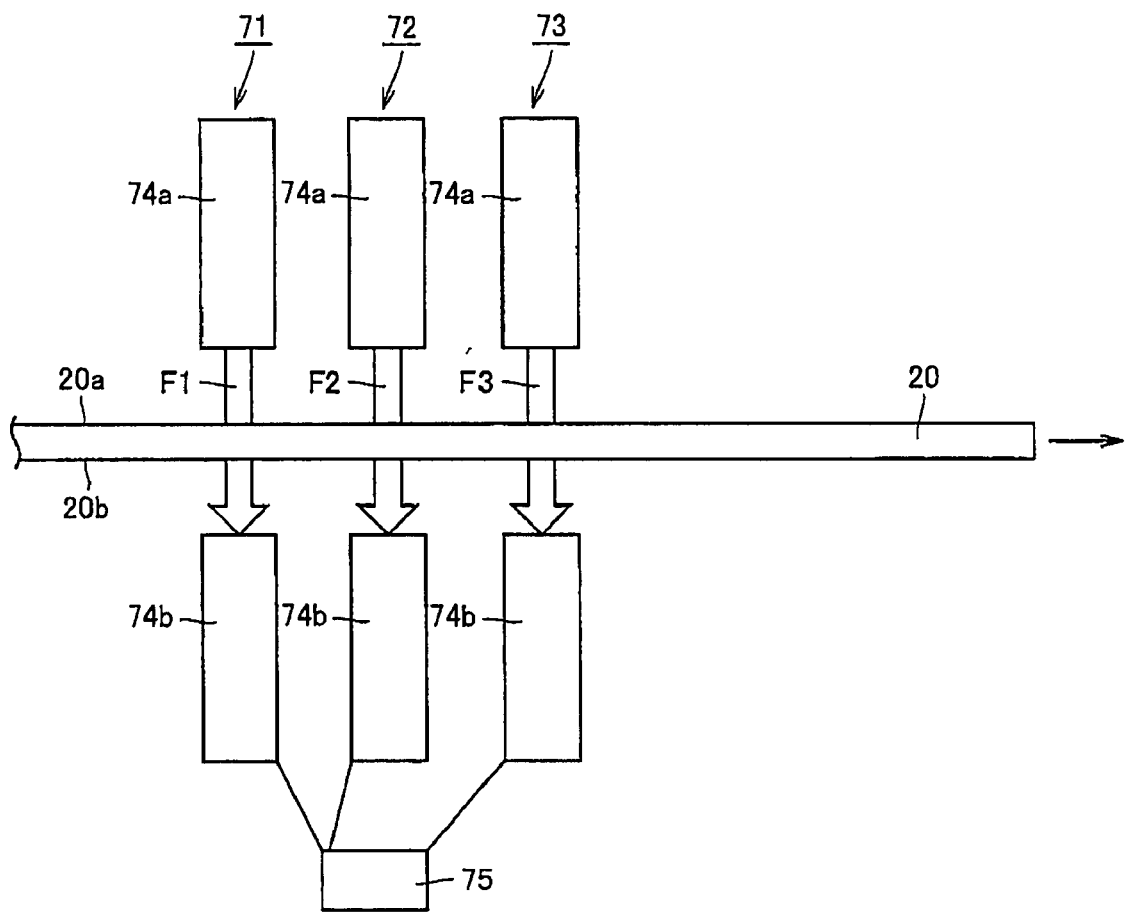
FIG. 20 schematically shows a configuration of the present superconducting wire inspection apparatus in an eighth embodiment.

FIG. 20 schematically shows a configuration of the present superconducting wire inspection apparatus in an eighth embodiment. With reference to FIG. 20, the present embodiment provides the superconducting wire inspection apparatus including the optical inspection apparatus indicated in any of the first to fourth embodiments plus three barycenter measuring devices 71-73. Barycenter measuring device 71 is first arranged followed by barycenter measuring device 72 and then barycenter measuring device 73 in the longitudinal direction of superconducting wire 20, and each barycenter measuring device includes an illumination unit 74a for emitting a laser beam of light for illumination, and a photoreceptive unit 74b for receiving the laser beam of light emitted from illumination unit 74a. Illumination unit 74a is each arranged over front surface 20a of superconducting wire 20 and photoreceptive unit 74b is each arranged under back surface 20b of superconducting wire 20. A pair of illumination unit 74a and photoreceptive unit 74b is coaxially arranged. Furthermore, barycenter measuring devices 71-73 have a common computer 75 and have their respective photoreceptive units 74b each electrically connected to computer 75.

When barycenter measuring devices 71-73 are employed, superconducting wire 20 is inspected in a method as will be described hereinafter.

Figure 21:
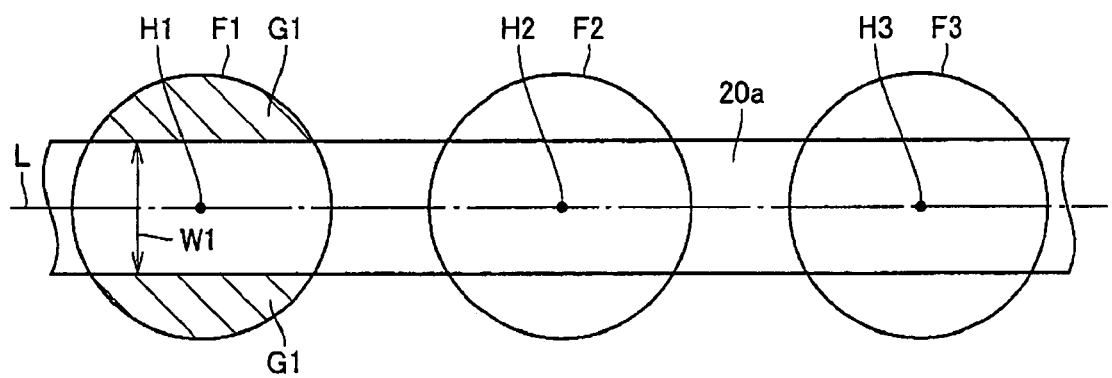
FIG. 21 is a diagram showing the position of a center of a superconducting wire which does not have deflection in the eighth embodiment.
Figure 22:
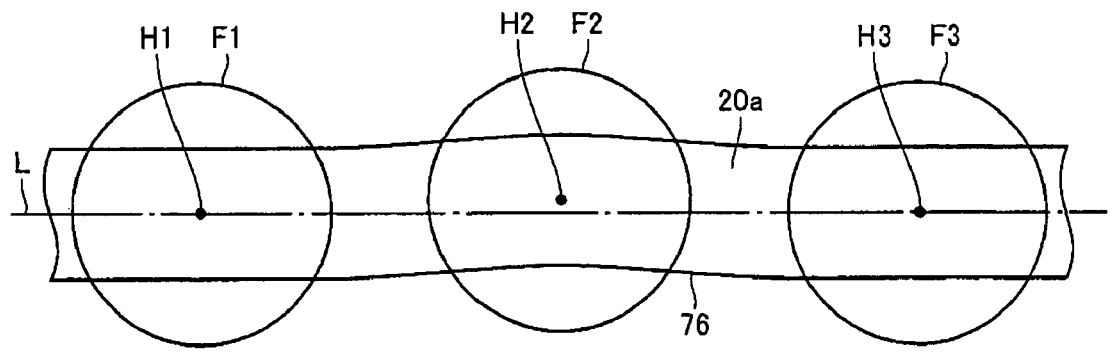
FIG. 22 is an upper view showing the position of a center of a superconducting wire which has deflection in the eighth embodiment.

FIG. 21 shows the position of a center of superconducting wire 20 when the wire does not have deflection, and FIG. 22 shows the position of a center of superconducting wire 20 when the wire has deflection.

With reference to FIGS. 20 and 21, illumination unit 74a of barycenter measuring device 71 emits a laser beam of light F1 to illuminate superconducting wire 20 at front surface 20a. Note that the laser beam of light F1 forms a spot having a diameter larger than the width of superconducting wire 20 (or a dimension thereof in the vertical direction as seen in FIG. 21). Of the laser beam of light F1, that illuminating superconducting wire 20 is reflected by front surface 20a and accordingly not received by photoreceptive unit 74b, and of the laser beam of light F1, only that which does not illuminate superconducting wire 20 (or that of a portion indicated in FIG. 21 by G1) is received by photoreceptive unit 74b. From a pattern G1 of light received by photoreceptive unit 74b, computer 75 measures and outputs the width of superconducting wire 20 at a position exposed to the laser beam of light F1, and a position H1 of a center (or a barycenter) of the wire as seen widthwise.

Barycenter measuring devices 72 and 73 follow the principle similar to that of barycenter 71 to measure and output widths of superconducting wire 20 at positions exposed to beams of light F2 and F3, respectively, and positions H2 and H3 of centers of the wire 20 as seen widthwise.

Herein if superconducting wire 20 does not have displacement as seen widthwise (or is defectless) between the position exposed to the laser beam of light F1 and that exposed to the laser beam of light F3, then the positions of centers H1-H3 located the positions exposed to the laser beams of light F1-F3, respectively, are all located on a straight line L parallel to the longitudinal direction of superconducting wire 20. In contrast, as shown in FIG. 22, for example if superconducting wire 20 flexes 76 or has a similar defect between the position exposed to the laser beam of light F1 and that exposed to the laser beam of light F3 and thus has displacement as seen widthwise, then at least one of the positions of centers H1-H3 (in the figure, the position of a center H2) deviates from straight line L. Consequently from the positions of centers H1-H3 a defect of front surface 20a of superconducting wire 20 is detected.

In the present embodiment the inspection apparatus further includes barycenter measuring devices 71-73 aligned in the longitudinal direction of superconducting wire 20 to measure a center of superconducting wire 20 as seen widthwise.

In the present embodiment the inspection method further includes the steps of: measuring the position of a center H1 of superconducting wire 20, as seen widthwise, at a position exposed to the laser beam of light F1; measuring the position of a center H2 of superconducting wire 20, as seen widthwise, at a position which is different in the longitudinal direction of the wire from the position exposed to the laser beam of light F1 and is exposed to the laser beam of light F2; and measuring the position of a center H3 of superconducting wire 20, as seen widthwise, at a position which is different in the longitudinal direction of the wire from the positions exposed to the laser beams of light F1 and F2 and is exposed to the laser beam of light F3.

Thus whether the positions of centers H1-H3 are all located on straight line L can be determined to measure whether a superconducting wire has deformation large in periodicity as seen in widthwise (e.g., deflection, waviness, swelling and the like). This in combination with the optical inspection apparatuses of the first to fourth embodiments allows a variety of types of defects to be detected and an inspection process to be performed more efficiently.

Furthermore, barycenter measuring devices 71-73 allow a pattern of light received by photoreceptive unit 74b to be used to detect how superconducting wire 20 varies widthwise at positions exposed to the laser beams of light F1-F3.

Note that while in the present embodiment barycenter measuring devices 71-73 measure the position of a center by a pattern of light received by photoreceptive unit 74b, the principle of the barycenter measuring device is not limited thereto; the barycenter measuring device may be any that measures the position of a center of superconducting wire 20 as seen widthwise.

Furthermore in the present embodiment the function as computer 75 may be fulfilled by computer 5 (FIG. 3). In that case, photoreceptive unit 74b is each electrically connected to computer 5. This allows a single computer to be used to conduct an inspection.

Furthermore, while in the first to eighth embodiments a multi-filamentary, superconducting oxide wire in the form of tape is inspected, a monofilamentary, superconducting oxide wire having a single, oxide superconductor filament covered with a sheath to provide a monofilamentary structure may be inspected. Furthermore, other than the superconducting wire in the form of tape, an unrolled and thus round superconducting wire may be inspected.

Furthermore while in the first to eighth embodiments a superconducting wire of a bismuth-based oxide is inspected, a superconducting wire of a yttrium-based oxide may be inspected, or a metal-based superconducting wire may be inspected. The present invention is broadly applicable to inspecting superconducting wires having any geometries.

Ninth Embodiment

Figure 23:
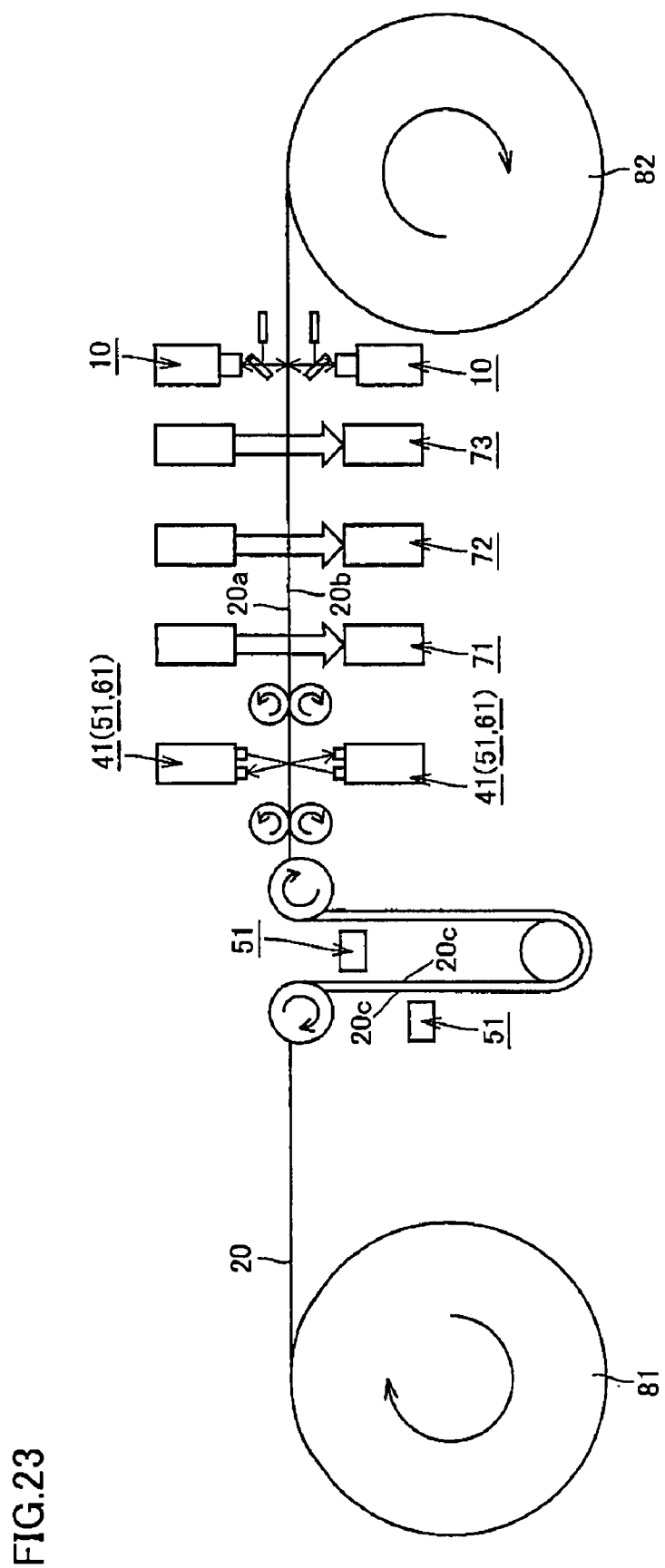
FIG. 23 conceptually shows the present superconducting wire inspection apparatus in a ninth embodiment.

FIG. 23 conceptually shows a superconducting wire inspection apparatus in the present embodiment. With reference to FIG. 23, the present embodiment provides the inspection apparatus including a feed reel 81, a take up reel 82, optical inspection apparatus 10 of the first embodiment, barycenter measuring devices 71-73 of the eighth embodiment, two laser displacement sensors 41 of the fifth embodiment, and eddy current displacement sensor 51 of the sixth embodiment. In the present embodiment the superconducting wire inspection apparatus feeds superconducting wire 20 from feed reel 81 to take up reel 82 and therebetween conducts a variety of inspections (an in-line inspection).

Initially, eddy current displacement sensor 51 arranged to face opposite sides of superconducting wire 20 measures superconducting wire 20 to measure how its end surface 20c is displaced for example to inspect whether superconducting wire 20 bends or has a similar defect or not. Then, laser displacement sensor 41 arranged to face each of front and back surfaces 20a and 20b of superconducting wire 20 measures displacement of superconducting wire 20 in the direction of the thickness thereof for example to inspect whether superconducting wire 20 has blister or a similar defect or not. Laser displacement sensor 41 may be replaced with eddy current displacement sensor 51 or contact displacement sensor 61 of the seventh embodiment. Superconducting wire 20 is then inspected by the three barycenter measuring devices 71-73 for example for deflection large in periodicity. Furthermore, superconducting wire 20 is also inspected for whether it deforms or not as seen widthwise. Superconducting wire 20 is then inspected by optical inspection apparatus 10 arranged to face each of front and back surfaces 20s and 20b of superconducting wire 20 for whether front and back surfaces 20a and 20b have a pinhole or a similar defect or not. Subsequently, superconducting wire 20 is taken up by take up reel 82.

Thus combining the inspection apparatuses of the first to eighth embodiments together as appropriate allows superconducting wire 20 to be inspected for a variety of defects, and the inspection process to be performed more efficiently.

Hereinafter examples of the present invention will be described.

FIRST EXAMPLE

In the present example a test employing pressurized nitrogen and the present apparatus and method of inspecting a superconducting wire were compared and how effective the present (optical) inspection apparatus and method is has been confirmed. More specifically, a superconducting wire was fabricated in the following method:

A powdery source material of $Bi_2CO_3$, PbO, $SrCO_3$, $CaCO_3$ and CuO was prepared to have an atomic ratio of Bi:Pb:Sr:Ca:Cu=1.8:0.3:1.9:2.0:3.0. The powdery source material was thermally treated and pulverized repeatedly to provide powder formed of a Bi2223 phase and a non-superconducting phase. The powder was then packed in a silver pipe which was in turn drawn to obtain a mono-filamentary clad wire. Then 61 such clad wires were bundled together and thus inserted into a silver pipe which was in turn drawn. A multi-filamentary wire having the powdery source material packed filamentarily was thus obtained. The multi-filamentary wire was then rolled to obtain a multi-filamentary wire in the form of tape having a silver ratio of 1.5, 61 filaments, a width of 4.2 mm, a thickness of 0.24 mm, and a length of 400 m. The multi-filamentary wire in the form of tape was then placed in the atmosphere of 840° C. and thermally treated for 50 hours, and thereafter cooled to room temperature and then again rolled at a draft of 8%. Subsequently the multi-filamentary wire was then placed in the atmosphere of 835° C. and again thermally treated for 50 hours to obtain a superconducting wire.

Figure 24:
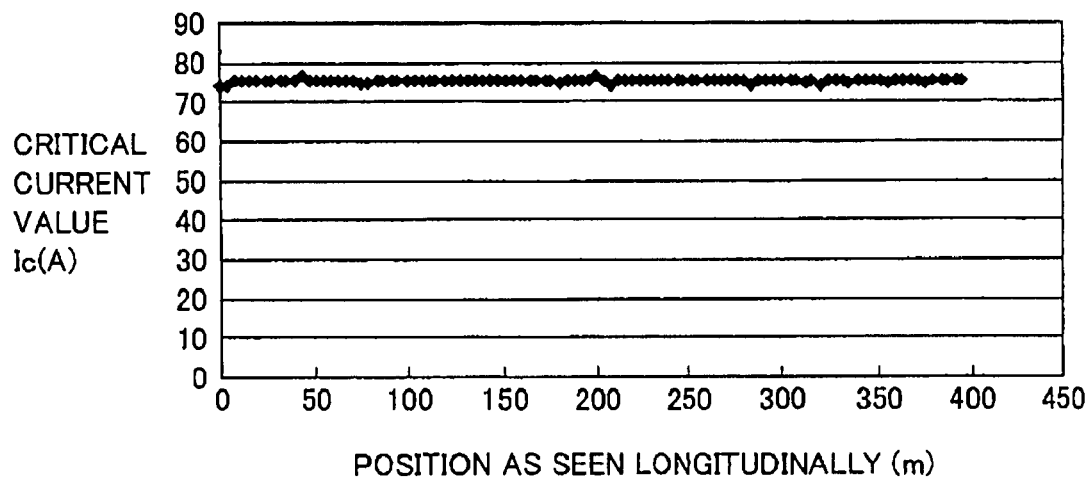
FIG. 24 represents a distribution of a critical current value of a superconducting wire, as seen longitudinally, in a first example of the present invention.

The superconducting wire obtained in the above method was then inspected longitudinally at intervals of 4 m for how its critical current value distributes as seen longitudinally. The critical current value is a value provided when a voltage of 1 µV is applied per 1 cm. A result of measuring the critical current value showed that, as shown in FIG. 24, the superconducting wire as seen longitudinally provides a critical current distributed substantially uniformly.

Then whether the superconducting wire had a surface with a flaw, a discolored portion, a pinhole and/or a similar defect was visually inspected to find that the wire had a surface with 17 defects having a diameter equal to or larger than 100 µm.

Subsequently the superconducting wire was inspected in a conventional method, i.e., underwent a test employing pressurized nitrogen. The test was conducted a plurality of times repeatedly to cause the wire to balloon to inspect whether the wire has a defect or not. Table 1 shows a relationship between how many times the test was conducted and the number of portions ballooned. Furthermore, immediately after the test was first conducted, the wire was inspected longitudinally at intervals of 4 m for how its critical current value distributes as seen longitudinally. The result was shown in FIG. 25.

TABLE 1

| How many times the test employing pressurized nitrogen was conducted | The number of portions ballooned |
|---|---|
| once | 3 |
| twice | 3 |
| 5 times | 5 |
| 10 times | 9 |

Figure 25:
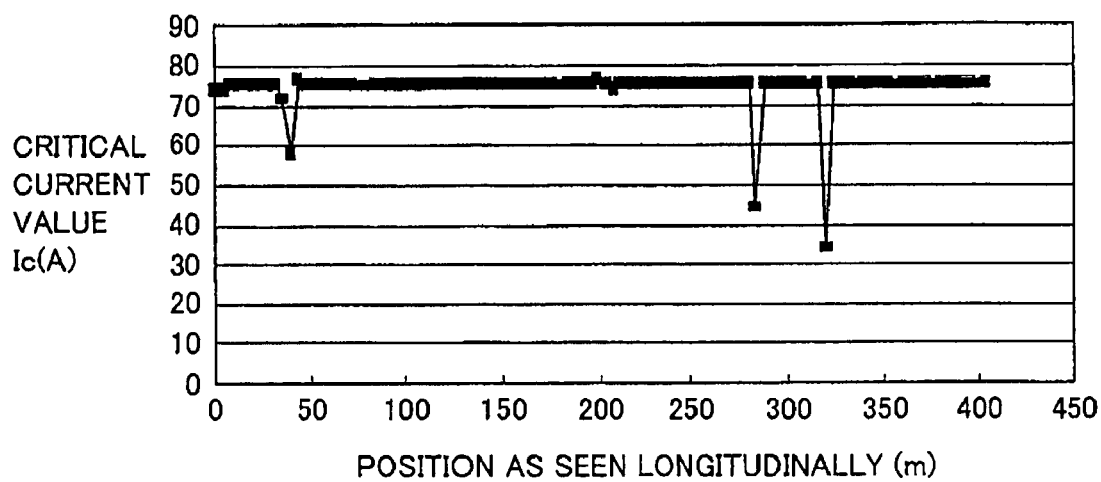
FIG. 25 represents a distribution of a critical current value of a superconducting wire, as seen longitudinally, in the first example of the present invention immediately after a test employing pressurized nitrogen is conducted for a first time.

With reference to Table 1 and FIG. 25, immediately after the test employing pressurized nitrogen was first conducted, the wire had ballooning at locations of approximately 40 m, approximately 280 m and approximately 320 m as seen longitudinally. In other words, when the test was conducted once, only three of 17 defects were detected. Furthermore, when the test was conducted ten times, only nine of the 17 defects were detected. This shows that the test employing pressurized nitrogen does not allow all defects to be detected.

Subsequently the superconducting wire inspection apparatus and method indicated in the first embodiment was employed to inspect whether there is a defect or not. The 17 defects were all detected. It can thus be seen that the present superconducting wire inspection apparatus and method can inspect a superconducting wire having a small defect with higher sensitivity than the conventional test employing pressurized nitrogen.

SECOND EXAMPLE

Figure 26:
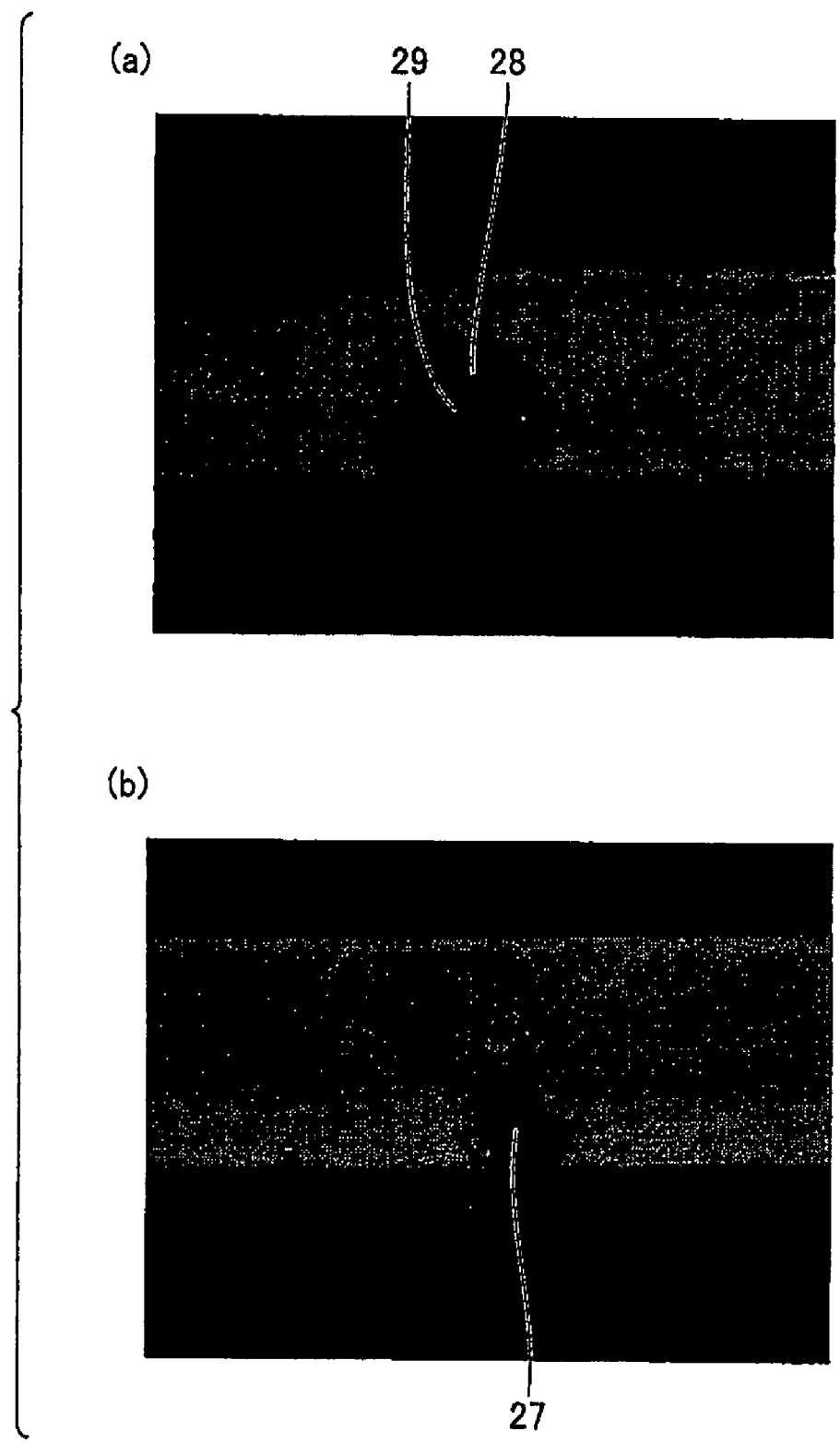
FIG. 26 is a photograph showing an enlarged view of a defect caused in a superconducting wire in a second example of the present invention. More specifically.

In the present example was examined how it is effective that a superconducting wire is illuminated by an illumination unit implemented by a coaxial illumination unit and how it is effective that the superconducting wire is illuminated by an illumination unit implemented by an oblique illumination unit. More specifically, a method similar to that described in the first example was employed to fabricate a superconducting wire. The obtained superconducting wire was visually observed to confirm that it had discolored portion 28 and pinhole 29 as shown in FIG. 26(a) and flaw 27 in a surface as shown in FIG. 26(b). Subsequently the superconducting wire was inspected with the following three inspection apparatuses for the defects. The result was indicated in Table 2.

Inspection apparatus A: the inspection apparatus configured as described in the first embodiment (an inspection apparatus including a coaxial illumination unit).

Inspection apparatus B: the inspection apparatus configured as described in the second embodiment (an inspection apparatus including an oblique illumination unit).

Inspection apparatus C: an inspection apparatus including an illumination unit implemented by domed illumination. Note that domed illumination is a type of illumination optically less directional than an LED and emitting light over a broader range than the LED.

TABLE 2

| | Discolored portion & pinhole | Flaw in surface |
|---|---|---|
| Inspection Apparatus A | 1 | 2 |
| Inspection Apparatus B | 2 | 1 |
| Inspection Apparatus C | 2 | 2 |

1: Detected with high sensitivity
2: Detected

Figure 27:
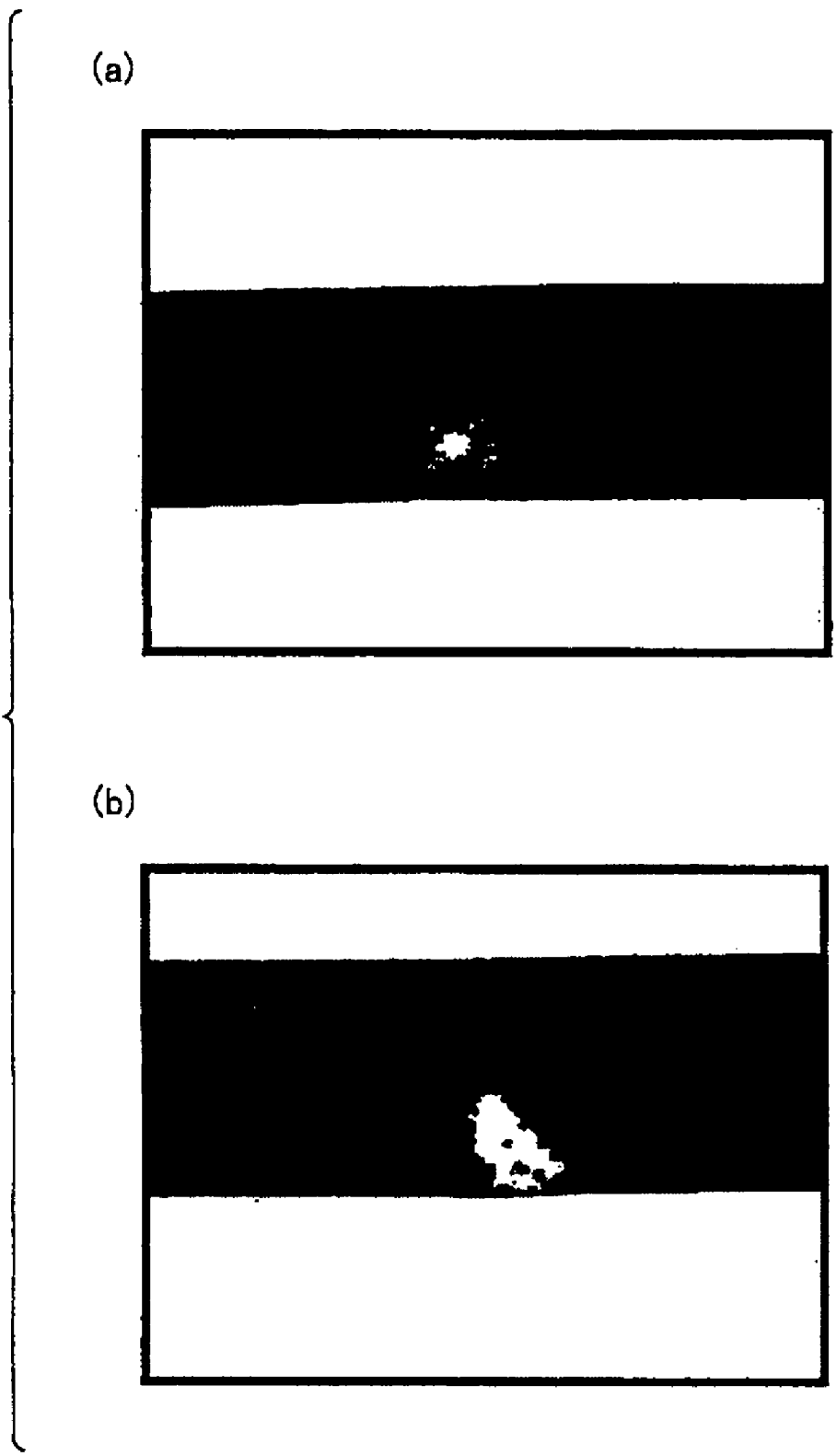
FIG. 27(a) is an image of the discolored portion and pinhole shown in FIG. 26(a), as photographed with an inspection apparatus A and binarized.
FIG. 27(b) is an image of the flaw in the surface shown in FIG. 26(b), as photographed with an inspection apparatus B and binarized.

With reference to Table 2, inspection apparatuses A-C all successfully detected the defects. In particular, inspection apparatus A was able to detect discoloration of a surface and a pinhole with high sensitivity. Inspection apparatus A clearly detected discolored portion 28 and pinhole 29 of FIG. 26(a), as shown in FIG. 27(a). Furthermore, in particular, inspection apparatus B was able to detect a flaw in a surface with high sensitivity. Inspection apparatus B clearly detected flaw 27 in a surface as shown in FIG. 26(b), as shown in FIG. 27(b).

THIRD EXAMPLE

In the present example, how the contact displacement sensor indicated in the seventh embodiment is effective was confirmed. More specifically, initially the following method was employed to fabricate a superconducting wire.

A powdery source material of $Bi_2CO_3$, PbO, $SrCO_3$, $CaCO_3$ and CuO was prepared to have an atomic ratio of Bi:Pb:Sr:Ca:Cu=1.8:0.3:1.9:2.0:3.0. The powdery source material was thermally treated and pulverized repeatedly to provide, powder formed of a Bi2223 phase and a non-superconducting phase. The powder was then packed in a silver pipe which was in turn drawn to obtain a mono-filamentary clad wire. Then 61 such clad wires were bundled together and thus inserted into a silver pipe which was in turn drawn. A multi-filamentary wire having the powdery source material packed filamentarily was thus obtained. The multi-filamentary wire was then rolled to obtain a multi-filamentary wire in the form of tape having a silver ratio of 2.5, 61 filaments, a width of 4.0 mm, a thickness of 0.26 mm, and a length of 1,300 m. The multi-filamentary wire in the form of tape was then placed in the atmosphere of 840° C. and thermally treated for 50 hours, and thereafter cooled to room temperature and then again rolled at a draft of 10%. As a result a multi-filamentary wire having a width of 4.2 mm and a thickness of 0.24 mm was obtained. Subsequently the multi-filamentary wire was placed in the atmosphere of 835° C. and again thermally treated for 50 hours to obtain a superconducting wire.

Subsequently the optical inspection apparatus and method described in the first embodiment was employed to inspect whether the superconducting wire had a defect or not. There was not detected a pinhole, a flaw in a surface, or a similar defect. Subsequently the contact displacement sensor described in the seventh embodiment and an inspection method employing the same were employed to measure displacement of the superconducting wire in the direction of the thickness thereof at intervals of 2 mm as seen longitudinally. The result is indicated in FIG. 28.

Figure 28:
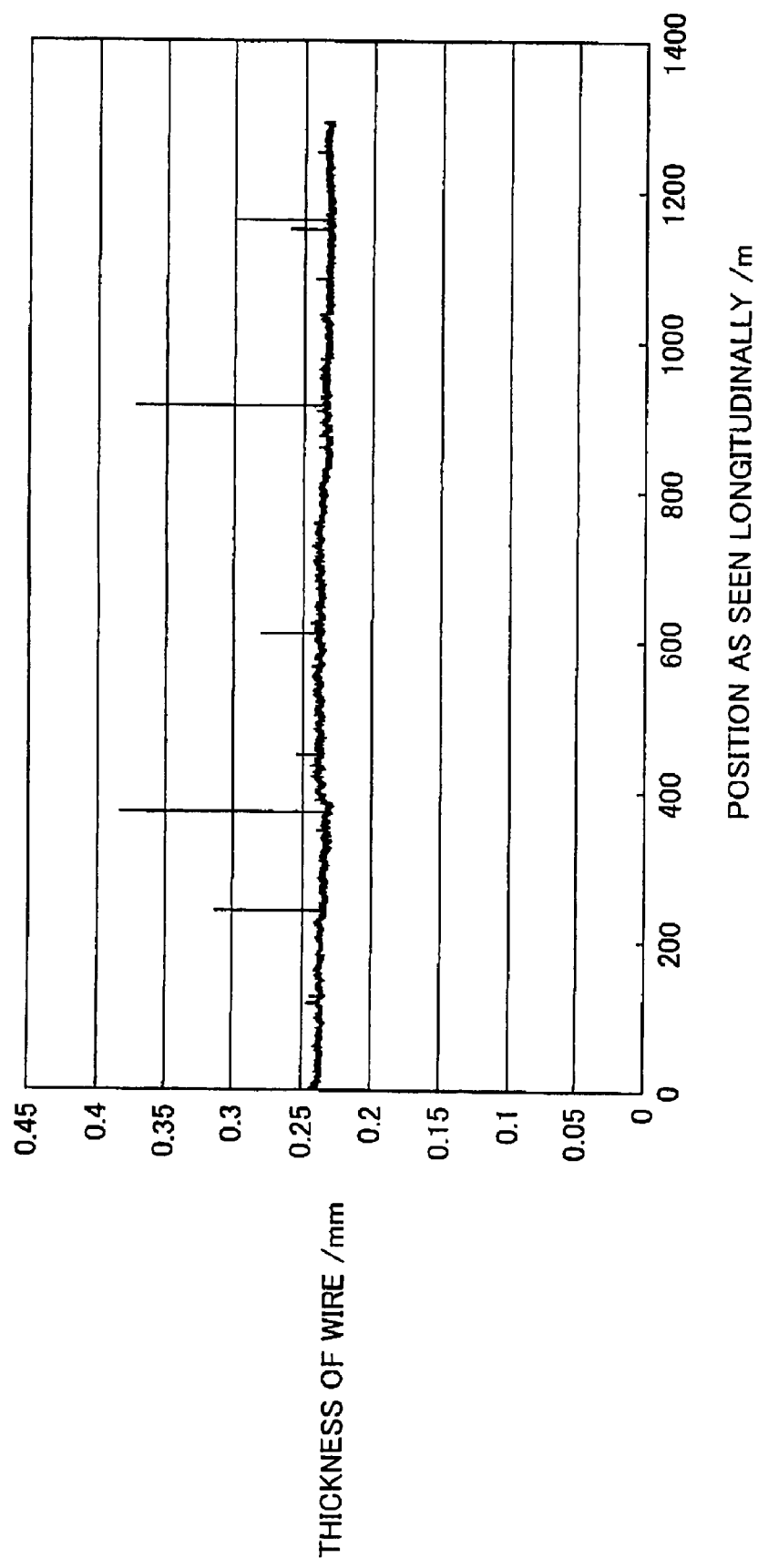
FIG. 28 shows displacement of a superconducting wire in thickness as seen longitudinally, as measured with a contact displacement sensor in a third example.

With reference to FIG. 28, that the wire had a thickness exceeding 0.25 mm at seven locations, was detected. After the measurement these locations were visually observed to confirm a blister caused by the thermal treatment. The blister is a defective portion contributing to reduced superconducting current.

From the above result it is found that the eddy current displacement sensor of the present invention allows a blister or a similar defect to be detected with high precision.

FOURTH EXAMPLE

In the present example, how the laser displacement sensor described in the fifth embodiment is effective was confirmed. More specifically, the laser displacement sensor described in the fifth embodiment and an inspection method employing the same were employed to inspect superconducting wire 20 fabricated in the third example for displacement, as seen widthwise, at intervals of 2 mm as seen longitudinally. The result is indicated in FIG. 29.

Figure 29:
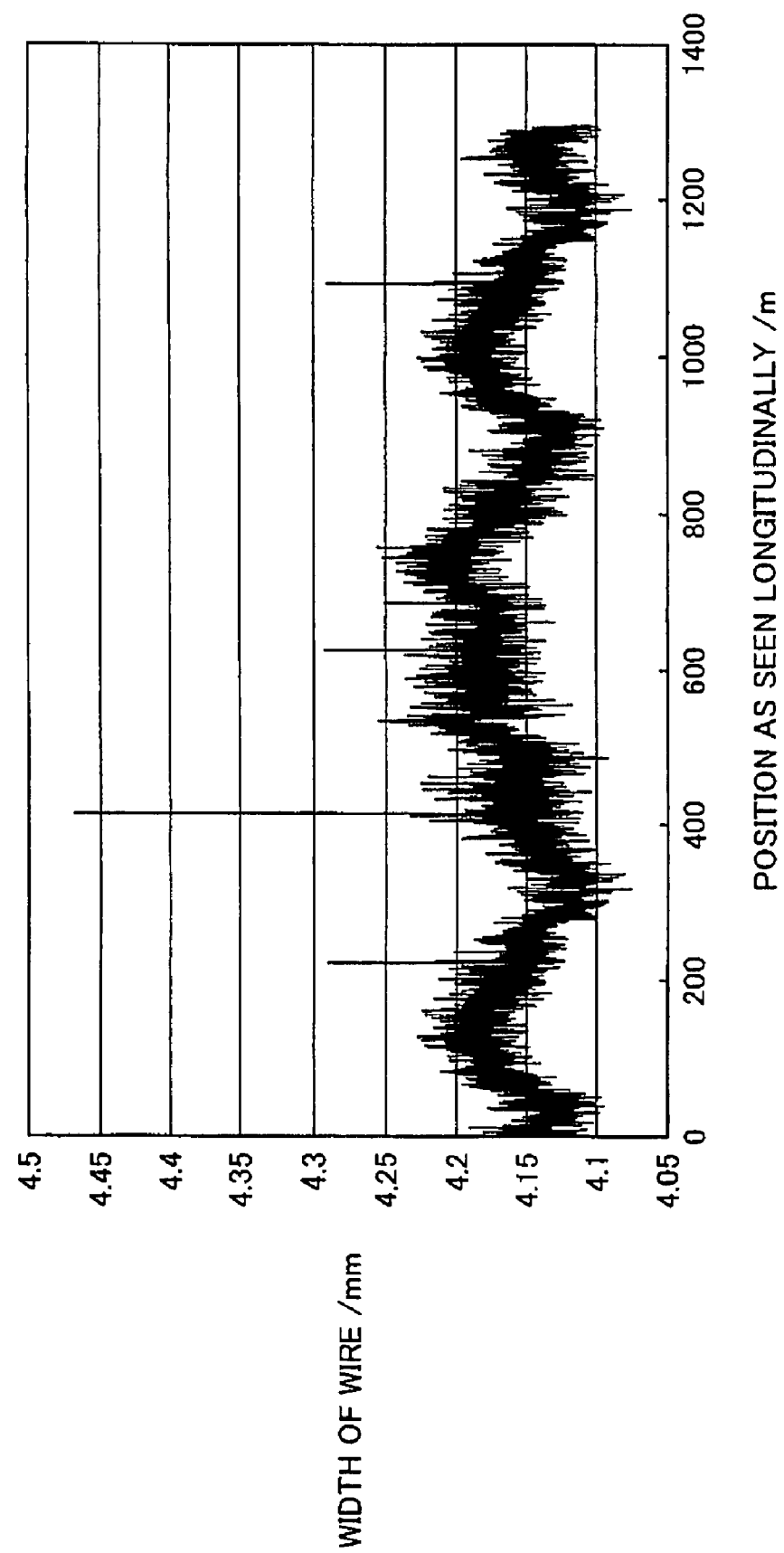
FIG. 29 shows displacement of a superconducting wire in width as seen longitudinally, as measured with a laser displacement sensor in a fourth example.

With reference to FIG. 29, that the wire had a width exceeding 4.25 mm at four locations, was detected. After the measurement these locations were visually observed to confirm that the wire was locally increased in width.

From the above result it is found that the laser displacement sensor of the present invention allows widthwise distortion or a similar defect to be detected with high precision.

FIFTH EXAMPLE

In the present example was confirmed how the barycenter measuring device described in the eighth embodiment is effective. More specifically, the three barycenter measuring devices described in the eighth embodiment and an inspection method employing the same were employed to measure the position of a center of superconducting wire 20 produced in the third example as seen widthwise to output a difference between the positions of centers as calculated by two barycenter measuring devices located at opposite sides (barycenter measuring devices 71 and 73 as seen in FIG. 20) and that of a center as calculated by a centered barycenter measuring device (barycenter measuring device 72 as seen in FIG. 20). The result is indicated in FIG. 30.

Figure 30:
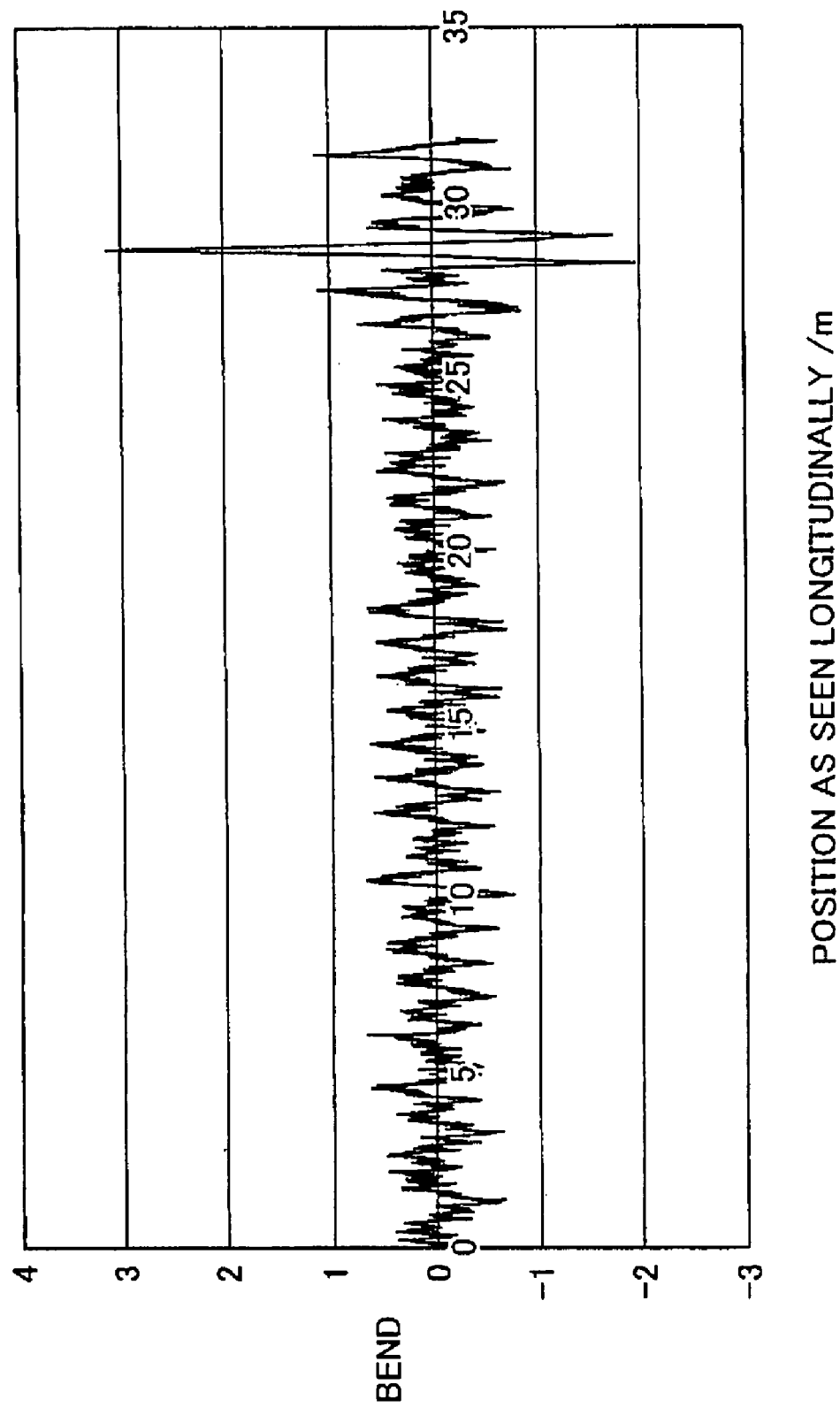
FIG. 30 represents how a difference between the positions of centers of a superconducting wire calculated by two barycenter measuring devices disposed at opposite sides of the wire and that of a center of the wire calculated by a center measuring device, as measured with such barycenter measuring devices in a fifth example of the present invention, varies as seen longitudinally.

With reference to FIG. 30, that the wire had a peak at a site in a vicinity of 28 m was detected. After the inspection the site was observed to confirm that the wire had a bend having a radius of curvature equal to or larger than 20,000 m.

From the above result it is found that the barycenter measuring device of the present invention can detect a wire's bend large in periodicity with high precision.

It should be understood that the embodiments and examples disclosed herein are illustrative and not limitative in any respect. The scope of the present invention is defined by the terms of the claims, rather than the embodiments and examples above, and is intended to include any modifications within the scope and meaning equivalent to the terms of the claims.

INDUSTRIAL APPLICABILITY

The present invention is broadly applicable to inspecting superconducting wires having any geometries and is particularly suitable for inspecting a superconducting oxide wire in the form of tape.

The invention claimed is:

1. An apparatus inspecting a superconducting wire, comprising:
    an illumination unit emitting light to illuminate a superconducting wire;
    a photoreceptive unit receiving light from said superconducting wire; and
    an output unit accumulating and outputting a signal representing a quantity of light received by said photoreceptive unit;
    further comprising a laser displacement sensor including a laser light illumination unit emitting a laser beam of light to illuminate said superconducting wire while moving relative to said superconducting wire in a longitudinal direction of said superconducting wire, a laser light reception unit receiving a laser beam of light reflected by said superconducting wire, and an output unit associated with said laser displacement sensor and outputting information on displacement of said superconducting wire as based on at which position said laser light reception unit receives light.

2. The apparatus inspecting a superconducting wire according to claim 1, wherein said photoreceptive unit is a photoreceptive unit receiving a reflection of light, that mainly receives light reflected by said superconducting wire.

3. The apparatus inspecting a superconducting wire according to claim 1, wherein said photoreceptive unit is a photoreceptive unit receiving diffused light, that mainly receives light diffused by said superconducting wire.

4. The apparatus inspecting a superconducting wire according to claim 1, wherein said illumination unit emitting light in a direction normal to a outer surface of said superconducting wire to illuminate said outer surface of said superconducting wire.

5. The apparatus inspecting a superconducting wire according to claim 1, wherein said illumination unit is an oblique illumination unit emitting light in a direction forming an angle with a direction normal to a outer surface of said superconducting wire to illuminate said outer surface of said superconducting wire.

6. The apparatus inspecting a superconducting wire according to claim 1, comprising more than one apparatus recited in claim 1.

7. An apparatus inspecting a superconducting wire, comprising:
    an illumination unit emitting light to illuminate a superconducting wire;
    a photoreceptive unit receiving light from said superconducting wire;
    an output unit accumulating and outputting a signal representing a quantity of light received by said photoreceptive unit; and
    an output unit accumulating and outputting a quantity of light received by said photoreceptive unit, further comprising an eddy current displacement sensor including:
    an alternate current generation unit passing an alternate current through a coil associated with said eddy current displacement sensor; said coil associated with said eddy current displacement sensor and generating an eddy current in said superconducting wire while moving relative to said superconducting wire in a longitudinal direction of said superconducting wire; and an output unit associated with said eddy current displacement sensor and outputting information on displacement of said superconducting wire as based on such variation in how said coil associated with said eddy current displacement sensor oscillates that is caused as said eddy current is generated.

8. An apparatus inspecting a superconducting wire, comprising:
    an illumination unit emitting light to illuminate a superconducting wire;
    a photoreceptive unit receiving light from said superconducting wire;

an output unit accumulating and outputting a signal representing a quantity of light received by said photoreceptive unit; and further comprising a contact displacement sensor including a probe moving relative to said superconducting wire in a longitudinal direction of said superconducting wire in contact with said superconducting wire and also moving in accordance with displacement of said superconducting wire, an iron core attached to said probe, a coil associated with said contact displacement sensor and generating an induced electromotive force as said iron core moves, and an output unit associated with said contact displacement sensor and outputting information on displacement of said superconducting wire as based on said induced electromotive force.

9. An apparatus inspecting a superconducting wire, comprising:

an illumination unit emitting light to illuminate a superconducting wire;

a photoreceptive unit receiving light from said superconducting wire;

an output unit accumulating and outputting a signal representing a quantity of light received by said photoreceptive unit; and further comprising first to third barycenter measuring devices aligned in a longitudinal direction of said superconducting wire to measure a center of said superconducting wire as seen widthwise.

10. A method of inspecting a superconducting wire, comprising the steps of:

emitting light to illuminate a superconducting wire;
receiving light from said superconducting wire;
accumulating and outputting a signal representing a quantity of light received; and further comprising the steps of:
emitting a laser beam of light in a longitudinal direction of said superconducting wire to illuminate said wire;
receiving said laser beam of light reflected by said superconducting wire; and
outputting information on displacement of said superconducting wire as based on a position receiving said laser beam of light.

11. The method of inspecting a superconducting wire according to claim 10, wherein the step of receiving includes mainly receiving light reflected by said superconducting wire.

12. The method of inspecting a superconducting wire according to claim 10, wherein the step of receiving includes mainly receiving light diffused by said superconducting wire.

13. The method of inspecting a superconducting wire according to claim 10, wherein the step of emitting includes emitting light in a direction normal to a outer surface of said superconducting wire to illuminate said outer surface.

14. The method of inspecting a superconducting wire according to claim 10, wherein the step of emitting includes emitting light in a direction forming an angle with a direction normal to a outer surface of said superconducting wire to illuminate said outer surface.

15. A method of inspecting a superconducting wire, comprising:

emitting light to illuminate a superconducting wire;
receiving light from said superconducting wire;
accumulating and outputting a signal representing a quantity of light received; and further comprising the steps of:
employing a coil associated with an eddy current displacement sensor and receiving and passing an alternate current therethrough to generate an eddy current in said superconducting wire in a longitudinal direction of said superconducting wire; and
outputting information on displacement of said superconducting wire as based on such variation in how said coil associated with said eddy current displacement sensor oscillates that is caused as said eddy current is generated.

16. A method of inspecting a superconducting wire, comprising:

emitting light to illuminate a superconducting wire;
receiving light from said superconducting wire;
accumulating and outputting a signal representing a quantity of light received; and further comprising the steps of: moving a probe, having an iron core attached thereto, relative to said superconducting wire in contact with said superconducting wire in a longitudinal direction of said superconducting wire, and also allowing said probe to move in accordance with displacement of said superconducting wire; and generating an induced electromotive force in a coil, which is associated with a contact displacement sensor, as said iron core moves, and outputting information on displacement of said superconducting wire as based on said induced electromotive force.

17. A method of inspecting a superconducting wire, comprising:

emitting light to illuminate a superconducting wire;
receiving light from said superconducting wire;
accumulating and outputting a signal representing a quantity of light received; and further comprising the steps of:
measuring a center of said superconducting wire, as seen widthwise, at a first position;
measuring a center of said superconducting wire, as seen widthwise, at a second position different from said first position in a longitudinal direction of said wire; and
measuring a center of said superconducting wire, as seen widthwise, at a third position different from said first and second positions in said longitudinal direction of said wire.

* * * * *